United States Patent
Matsunaga et al.

(10) Patent No.: US 8,329,929 B2
(45) Date of Patent: Dec. 11, 2012

(54) METAL COMPLEX

(75) Inventors: Tadafumi Matsunaga, Tsukuba (JP); Nobuyoshi Koshino, Tsukuba (JP); Hideyuki Higashimura, Tsukuba (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 533 days.

(21) Appl. No.: 12/530,413

(22) PCT Filed: Mar. 10, 2008

(86) PCT No.: PCT/JP2008/054328
§ 371 (c)(1), (2), (4) Date: Sep. 8, 2009

(87) PCT Pub. No.: WO2008/111567
PCT Pub. Date: Sep. 18, 2008

(65) Prior Publication Data
US 2010/0105853 A1    Apr. 29, 2010

(30) Foreign Application Priority Data
Mar. 9, 2007  (JP) ................. 2007-061007

(51) Int. Cl.
*C07F 15/00* (2006.01)
*C07F 1/08* (2006.01)
*C07F 5/06* (2006.01)
*C07F 7/00* (2006.01)

(52) U.S. Cl. ........ 556/138; 556/146; 556/110; 556/113; 556/45; 556/27; 556/42; 556/51; 556/57; 556/64; 556/81; 556/118; 556/136; 502/171; 502/150; 528/166; 528/210; 528/219; 528/395

(58) Field of Classification Search .................. 556/138, 556/136, 146, 110, 45
See application file for complete search history.

(56) References Cited

U.S. PATENT DOCUMENTS

2010/0105853 A1*  4/2010  Matsunaga et al. ........... 526/241
2010/0105909 A1*  4/2010  Matsunaga et al. ................ 546/6
2010/0129698 A1*  5/2010  Okada et al. ..................... 429/40

FOREIGN PATENT DOCUMENTS
EP           1380342 A1       1/2004

OTHER PUBLICATIONS

Lam, P.; Xu, J.X.; Chan, K.S., J. Org. Chem., 1996, 61, 8414-8418.*
Lam, P.; Feng, M.Q.; Chan, K.S., Tetrahedron, 1999, 8377-8384).*
Fennie et al., Tetrahedron, 2005, 61, 6249-6265.*
Fung Lam et al., "Synthesis of Dinucleating Phenanthroline-Based Ligands," Tetrahedron, 55 (1999), pp. 8377-8384.
Fung Lam et al., "Synthesis of Acyclic Dinucleating Phenanthroline-Pyridine and Phenanthroline-Phosphine Ligands," Tetrahedron Letters, 1995, pp. 6261-6262, vol. 36, No. 35.
Edited by Shadun Hojin Nippon Kagaku Gakkai, Kagaku Sosetsu No. 34 Shokubai Sekkei, Japan Scientific Societies Press, Aug. 1, 1982, pp. 176-189.
Susumu Kitagawa et al., "Functional Porous Coordination Polymers," Angewandte Chemie, 2004, pp. 2334-2375, vol. 43.
Jian Gao et al., "Catalytic asymmetric cyclopropanation at a chiral platform," Org. Biomol. Chem., 2005, pp. 2126-2128, vol. 3.
Zenghe Liu et al., "Schiff Base Complexes of Vanadium (III, IV, V) as Catalysts for the Electroreduction of O2 to H2O in Acetonitrile," Inorg. Chem., 2001, pp. 1329-1333, vol. 40.

* cited by examiner

Primary Examiner — Rip A. Lee
(74) Attorney, Agent, or Firm — Sughrue Mion, PLLC

(57) ABSTRACT

A metal complex represented by the following formula (1):

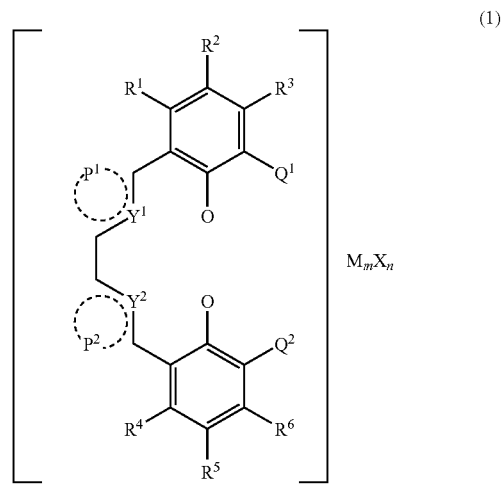

wherein $R^1$ to $R^6$ each independently represent a hydrogen atom or a substituent; $Y^1$ and $Y^2$ each independently represent any one of the following groups:

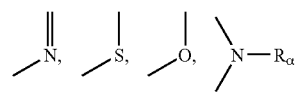

wherein $R_\alpha$ represents a hydrogen atom or a hydrocarbon group having 1 to 4 carbon atoms; $P^1$ and $P^2$ each represent a group of atoms necessary for forming a heterocyclic ring together with $Y^1$ or $Y^2$ and the two carbon atoms at a position adjacent to $Y^1$ or $Y^2$; $P^1$ and $P^2$ may be linked to each other to form a ring; M represents a transition metal element or typical metal element; m represents 1 or 2; X represents a counter ion or a neutral molecule; n represents the number of X's in the complex, and an integer of 0 or more; and $Q^1$ and $Q^2$ each independently represent an aromatic heterocyclic group.

20 Claims, 3 Drawing Sheets

METAL COMPLEX

CROSS REFERENCE TO RELATED APPLICATION

This application is a National Stage of International Application No. PCT/JP2008/054328 filed Mar. 10, 2008, claiming priority based on Japanese Patent Application No. 2007-061007, filed Mar. 9, 2007, the contents of all of which are incorporated herein by reference in their entirety.

TECHNICAL FIELD

The present invention relates to a metal complex, and more specifically, to a metal complex useful as a catalyst.

BACKGROUND ART

Metal complexes each act as a catalyst in a redox reaction involving electron transfer such as an oxygenation reaction, an oxidative coupling reaction, a dehydrogenation reaction, a hydrogenation reaction, an oxide decomposition reaction, or an electrode reaction, and are each used in the production of an organic compound or polymer compound. In addition, each of the metal complexes has been recently used as a phosphorescent complex for an organic EL material. Further, the metal complexes are used in various applications including additives, modifiers, cells, and sensor materials.

In particular, as for a redox reaction catalyst, Schiff base type metal complexes are known to have the highly-active and highly-selective catalytic abilities. For example, Org. Biomol. Chem., 2005, 3, 2126 describes that an optically active Schiff base type complex is used as a catalyst to oxidize the double bond of styrene so that an asymmetric cyclopropanation reaction may occur, and the asymmetric reaction may proceed favorably. In addition, Inorg. Chem., 2001, 40, 1329 describes that the production of water by the electrolytic reduction of oxygen is performed by using a Schiff base type metal complex.

However, the metal complex disclosed in Org. Biomol. Chem., 2005, 3, 2126 involves the possibility that when the metal complex is used as a catalyst, the catalyst is destabilized under heating, and hence its activity lowers. Further, the catalyst is used in a limited range of applications owing to the possibility that the catalyst is destabilized also in the presence of a strong acid. As described above, a metal complex that has been conventionally disclosed has the potential to be decomposed under some reaction conditions.

DISCLOSURE OF INVENTION

According to the present invention, there can be provided a metal complex excellent in stability and useful as a redox reaction catalyst or the like.

According to the present invention, there is provided the following means:

(1) A metal complex represented by the following formula (1):

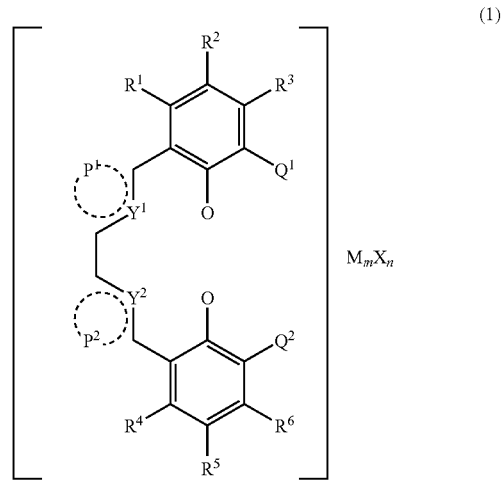

wherein $R^1$ to $R^6$ each independently represent a hydrogen atom or a substituent; $R^1$ and $R^2$, $R^2$ and $R^3$, $R^4$ and $R^5$, and/or $R^5$ and $R^6$ may be linked to each other to form a ring; and $Y^1$ and $Y^2$ each independently represent any one of the following groups:

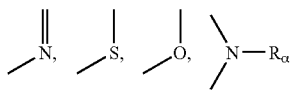

wherein $R_\alpha$ represents a hydrogen atom or a hydrocarbon group having 1 to 4 carbon atoms; $P^1$ represents a group of atoms necessary for forming a heterocyclic ring together with $Y^1$ and the two carbon atoms at a position adjacent to $Y^1$; $P^2$ represents a group of atoms necessary for forming a heterocyclic ring together with $Y^2$ and the two carbon atoms at a position adjacent to $Y^2$; $P^1$ and $P^2$ may be linked to each other to form a ring; M represents a transition metal element or typical metal element described in the periodic table; m represents 1 or 2; when m is 2, two M's may be the same as or different from each other; X represents a counter ion or a neutral molecule; n represents the number of X's in the complex, and an integer of 0 or more; when a plurality of X's are present, the X's may be the same as or different from each other; and $Q^1$ and $Q^2$ each independently represent an aromatic heterocyclic group.

(2) A metal complex represented by the following formula (2):

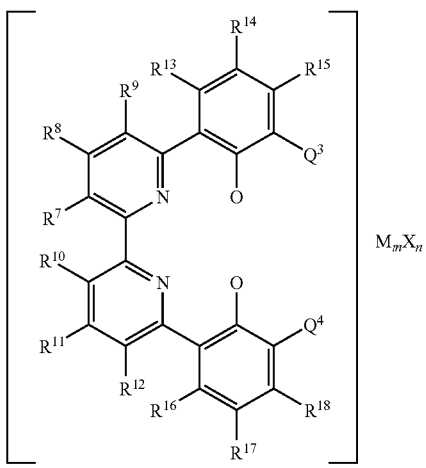

wherein $R^7$ to $R^{18}$ each independently represent a hydrogen atom or a substituent; $R^7$ and $R^{10}$, $R^7$ and $R^8$, $R^8$ and $R^9$, $R^9$ and $R^{13}$, $R^{10}$ and $R^{11}$, $R^{11}$ and $R^{12}$, $R^{12}$ and $R^{16}$, $R^{13}$ and $R^{14}$, $R^{14}$ and $R^{15}$, $R^{16}$ and $R^{17}$ and/or $R^{17}$ and $R^{18}$ may be linked to each other to form a ring; M represents a transition metal element or typical metal element described in the periodic table (IUPAC 2001); m represents an integer of 1 or 2; when m is 2, two M's may be the same as or different from each other; X represents a counter ion or a neutral molecule; n represents the number of X's in the complex, and an integer of 0 or more; when a plurality of X's are present, the X's may be the same as or different from each other; and $Q^3$ and $Q^4$ each independently represent an aromatic heterocyclic group.

(3) The metal complex according to the above (1) or (2), wherein, in the formula (1) or (2), m represents 2, and M represents a transition metal element belonging to Groups 3 to 9 described in the periodic table (IUPAC 2001).

(4) The metal complex according to the above (1) or (2), wherein, in the formula (1) or (2), m represents 1.

(5) A polymer, comprising a residue of the metal complex represented by the formula (1) or (2).

(6) The polymer according to the above (5), comprising the residue of the metal complex represented by the formula (1) or (2) as a repeating unit.

(7) A catalyst obtained by using the metal complex according to any one of the above items (1) to (4) and/or the polymer according to the above (5) or (6).

Other and further features and advantages of the invention will appear more fully from the following description, appropriately referring to the accompanying drawings.

BEST MODE FOR CARRYING OUT THE INVENTION

Figure 1:
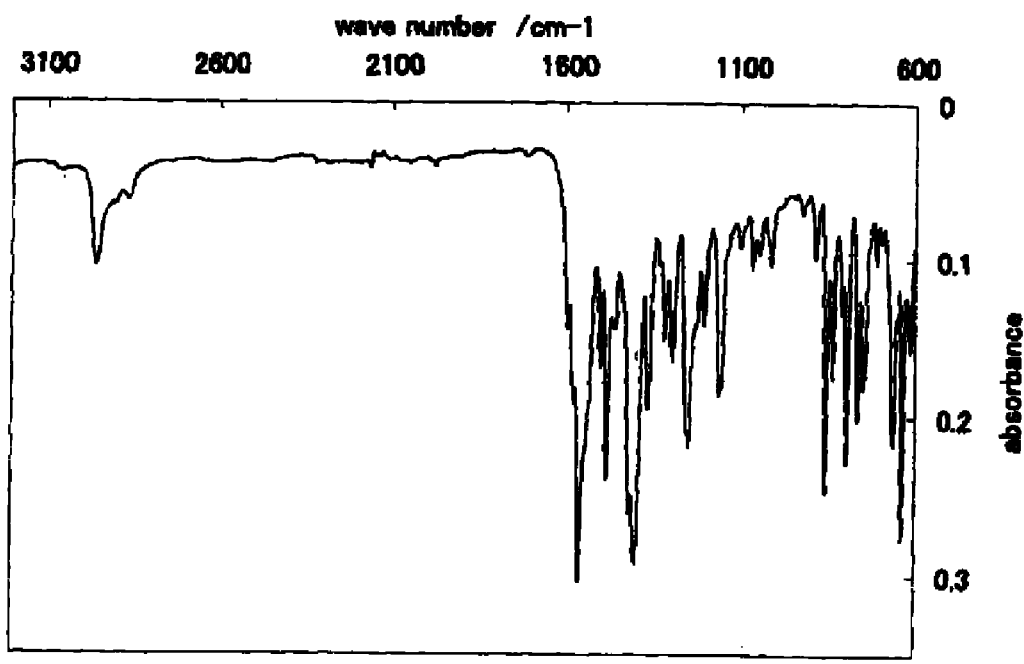
FIG. 1 shows an IR absorption spectrum of Metal Complex (A).

The metal complex represented by the formula (1) as a first embodiment of the present invention is described.

The metal complex is a complex comprising a metal atom M as a transition metal atom element or typical metal element, and a ligand having four heteroatoms and two oxygen atoms. In addition, a bond that links an oxygen atom and the metal atom is a coordination bond or an ionic bond; when two metal atoms are present, the metal atoms may be coordinated with each other by bridge coordination. The term "transition metal" as used herein has the same meaning as that of a "transition element" described in p 1283 of "Chemistry Unabridged Dictionary" (edited by Michinori Ohki et al. and issued by Tokyo Kagaku Dojin on Jul. 1, 2005), and means to an element having an incomplete d or f subshell. It should be noted that the transition metal atom M in the present invention may be uncharged, or may be a charged ion; the same holds true for the typical metal atom M, and the typical metal atom M may be uncharged, or may be a charged ion.

Here, specific examples of the transition metal M include scandium, titanium, vanadium, chromium, manganese, iron, cobalt, nickel, copper, zinc, yttrium, zirconium, niobium, molybdenum, ruthenium, rhodium, palladium, silver, cadmium, hafnium, tantalum, tungsten, rhenium, osmium, iridium, platinum, gold, and mercury.

In addition, specific examples of the typical metal include aluminum, gallium, germanium, indium, tin, antimony, thallium, lead, and bismuth.

The metal complex represented by the formula (1) is preferably one represented by the formula (2).

In each of the formulae (1) and (2), when m represents 2, M suitably represents a metal atom selected from the transition metal atoms belonging to Groups 3 to 9 described in the periodic table. Two M's may be the same as or different from each other.

The transition metal atom M belonging to Groups 3 to 9, when m represents 2, represents preferably scandium, titanium, vanadium, chromium, manganese, iron, cobalt, yttrium, zirconium, niobium, molybdenum, ruthenium, rhodium, hafnium, tantalum, tungsten, rhenium, osmium, or iridium, more preferably titanium, vanadium, chromium, manganese, iron, cobalt, zirconium, niobium, molybdenum, ruthenium, or rhodium, and particularly preferably a transition metal belonging to Period 4, and specifically, titanium, vanadium, chromium, manganese, iron, or cobalt. In the present invention, as described above, the transition metal atom M may be a transition metal ion.

M described in the formulae (1) and (2), when m represents 1, represents one selected from the group consisting of the transition metal atoms and typical metal atoms, preferably aluminum, titanium, vanadium, chromium, manganese, iron, cobalt, nickel, copper, zinc, gallium, germanium, zirconium, niobium, molybdenum, ruthenium, rhodium, palladium, silver, cadmium, indium, tin, antimony, tantalum, tungsten, rhenium, osmium, iridium, platinum, or gold, more preferably aluminum, titanium, vanadium, chromium, manganese, iron, cobalt, nickel, copper, zinc, gallium, molybdenum, ruthenium, rhodium, palladium, silver, tungsten, rhenium, osmium, iridium, platinum, or gold, and particularly preferably a transition metal belonging to Period 4, and specifically, titanium, vanadium, chromium, manganese, iron, cobalt, nickel, copper, or zinc. In the present invention, as described above, M may represent an ion of a transition metal or a typical metal.

Next, the ligand of the metal complex represented by the above formula (1) is described. In the formula (1), $R^1$ to $R^6$ each independently represent a hydrogen atom or a substituent.

Here, specific examples of the substituent include: a halogeno group such as a fluoro group, a chloro group, a bromo group, and an iodo group; a hydroxyl group; a carboxyl group; a mercapto group; a sulfonic acid group; a nitro group; a phosphonic acid group; a silyl group having an alkyl group with 1 to 4 carbon atoms; a linear, branched, or cyclic saturated hydrocarbon groups each having a total carbon atoms of 1 to about 50, such as a methyl group, an ethyl group, a propyl group, an isopropyl group, a cyclopropyl group, a butyl group, an isobutyl group, a tert-butyl group, a pentyl group, a cyclopentyl group, a hexyl group, a cyclohexyl group, a norbornyl group, a nonyl group, a cyclononyl group, a decyl group, a 3,7-dimethyloctyl group, an adamantyl group, a dodecyl group, a cyclododecyl group, a pentadecyl group, an octadecyl group, and a docosyl group; a linear, branched, or cyclic alkoxy groups each having a total carbon atoms of 1 to about 50 such as a methoxy group, an ethoxy group, a propioxy group, a butoxy group, a pentyloxy group, a cyclohexyloxy group, a norbonyloxy group, a decyloxy group, and a dodecyloxy group; and aromatic groups each having a total carbon atoms of 6 to about 60 such as a phenyl group, a 4-methylphenyl group, a 1-naphthyl group, a 2-naphthyl group, and a 9-anthryl group.

$R^1$ to $R^6$ each preferably represent: a halogeno group such as a fluoro group, a chloro group, a bromo group, or an iodo group; a mercapto group; a hydroxyl group; a carboxyl group; a hydrocarbon group having a total carbon atoms of 1 to about 20 including exemplified by a methyl group, an ethyl group, a propyl group, an isopropyl group, a butyl group, a pentyl group, a tert-butyl group, a cyclohexyl group, a norbornyl group, or an adamantyl group; a linear, or branched alkoxy group having a total carbon atoms of 1 to about 10 including exemplified by a methoxy group, an ethoxy group, a propioxy group, a butoxy group, or a pentyloxy group; an aromatic group having a total carbon atoms of 6 to about 30 such as a phenyl group, a 1-naphthyl group, a 2-naphthyl group, and a 9-anthryl group; or a hydrogen atom.

More preferred is a chloro group, a bromo group, a hydroxy group, a carboxyl group, a methyl group, an ethyl group, a tert-butyl group, a cyclohexyl group, a norbornyl group, an adamantyl group, a methoxy group, an ethoxy group, a phenyl group, or a hydrogen atom.

$R^1$ and $R^2$, $R^2$ and $R^3$, $R^4$ and $R^5$, and/or $R^5$ and $R^6$ may be linked to each other to form a ring.

Here, examples of the ring include: hydrocarbon rings such as a cyclohexene ring, a benzene ring, a naphthalene ring, an anthracene ring, and an acenaphthene ring; and aromatic heterocyclic rings such as a furan ring and a thiophene ring.

It should be noted that the ring formed by the coupling of two substituents may further have a substituent, and examples of such substituent include substituents equivalent to above exemplary substituents.

$Y^1$ and $Y^2$ each independently represent any one of the following groups.

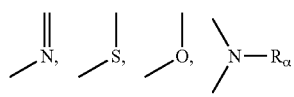

Herein, $R_\alpha$ represents a hydrogen atom or a hydrocarbon group having 1 to 8, preferably 1 to 4 carbon atoms.

The monovalent hydrocarbon group represented by $R^\alpha$ is the same as any one of the above exemplary substituents. $P^1$ and $P^2$ each independently represent a group of atoms necessary for forming a heterocyclic ring together with $Y^1$ and $Y^2$ and the two carbon atoms at positions adjacent to $Y^1$ and $Y^2$ (which may hereinafter be referred to as "$P^1$ and $P^2$ structure").

It should be noted that the two carbon atoms at adjacent positions do not include carbon atoms that can be included in $R^\alpha$. Specific examples of the heterocyclic ring include pyridine, pyrazine, pyrimidine, pyrrole, N-alkyl pyrrole, furan, thiophene, thiazole, imidazole, oxazole, benzimidazole, benzofuran, benzothiophene, isoquinoline, and quinazoline, preferably pyridine, pyrazine, pyrimidine, pyrrole, furan, thiophene, and N-alkylpyrrole, and more preferably pyridine, pyrrole, furan, and thiophene.

In addition, the $P^1$ and $P^2$ structures may be linked to each other to form a new ring, which preferably has a structure represented by any one of the following formulae (1-a) to (1-i), and more preferably has a structure represented by any one of the formulae (1-a) to (1-d).

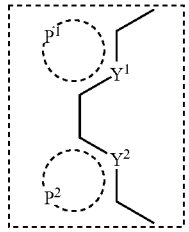

(1-a)

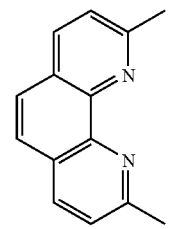

(1-b)

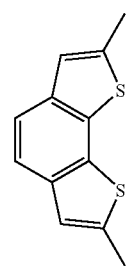

(1-c)

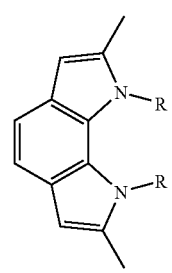

(1-d)
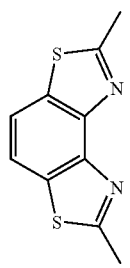

(1-e)
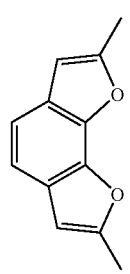

(1-f)
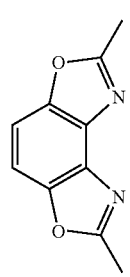

(1-g)
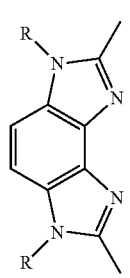

(1-h)
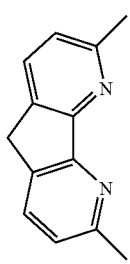

(1-i)
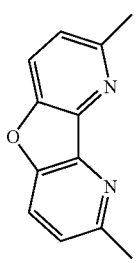

R represents a hydrogen atom or a hydrocarbon group having 1 to 30 carbon atoms.

It should be noted that each of the $P^1$ and $P^2$ structures may have a substituent, and examples of such substituent include substituents equivalent to the exemplary substituents applied to $R^1$ to $R^6$.

Substituents $Q^1$ and $Q^2$ represent an aromatic heterocyclic group. In the present invention, the aromatic heterocyclic group specifically refers to a pyridyl group, a pyrazyl group, a pyrimidyl group, a pyridazyl group, a pyrrolyl group, a furyl group, a thienyl group, a thiazolyl group, an imidazolyl group, an oxazolyl group, a triazolyl group, an indolyl group, a benzoimidazolyl group, a benzofuryl group, a benzothienyl group, a quinolyl group, an isoquinolyl group, a cinnolyl group, a phthalazyl group, a quinazolyl group, a quinoxanyl group, and a benzodiazyl group, preferably a pyridyl group, a pyrazyl group, a pyridazyl group, a pyrrolyl group, a furyl group, a thienyl group, a thiazolyl group, an indolyl group, and a benzoimidazolyl group, and more preferably a pyridyl group, a pyrrolyl group, a furyl group, a thienyl group, and a thiazolyl group.

In addition, these rings may further have substituents and the substituents include substituents equivalent to the exemplary substituents of $R^1$ to $R^6$.

The metal complex represented by the formula (1) preferably has a ligand structure obtained by combining those represented by the above specific examples of $P^1$ and $P^2$, and $Y^1$ and $Y^2$, and those represented by the above specific examples of $Q^1$ and $Q^2$.

Next, the metal complex of the present invention is preferably a metal complex represented by the formula (2). As described above, the ligand has at least two nitrogen atoms and two oxygen atoms as coordinating atoms. The ring may have a substituent, and $R^7$ to $R^{18}$ in the formula (2) each independently represent a hydrogen atom or a substituent.

Here, the substituent includes the same substituent represented by any one of $R^1$ to $R^6$ in the formula (1).

$Q^3$ and $Q^4$ represent an aromatic heterocyclic group. Specific examples of the aromatic heterocyclic group include a pyridyl group, a pyrazyl group, a pyrimidyl group, a pyridazyl group, a pyrrolyl group, a furyl group, a thienyl group, a thiazolyl group, an imidazolyl group, an oxazolyl group, a triazolyl group, an indolyl group, a benzoimidazolyl group, a benzofuryl group, a benzothienyl group, a quinolyl group, an isoquinolyl group, a cinnolyl group, a phthalazyl group, a quinazolyl group, a quinoxanyl group, and a benzodiazyl group, preferably a pyridyl group, a pyrazyl group, pyridazyl group, a pyrrolyl group, a furyl group, a thienyl group, a thiazolyl group, an indolyl group, and a benzoimidazolyl group, and more preferably a pyridyl group, a pyrrolyl group, a furyl group, a thienyl group, and a thiazolyl group. While, the aromatic heterocyclic group may be linked at any position of the rings, the aromatic heterocyclic group is preferably linked at ortho-position or meta-position with respect to hetero elements.

In addition, each of these aromatic heterocyclic groups $Q^3$ and $Q^4$ may further have substituents, and examples of such substituents include substituents equivalent to the exemplary substituents applied to $R^1$ to $R^6$ in the formula (1).

The metal complex represented by the formula (2) preferably has a ligand structure obtained by combining those represented by the above specific examples of $Q^3$ and $Q^4$. To be specific, the metal complex more preferably has any one of the following ligand structure structures (I) to (XII).

(I)
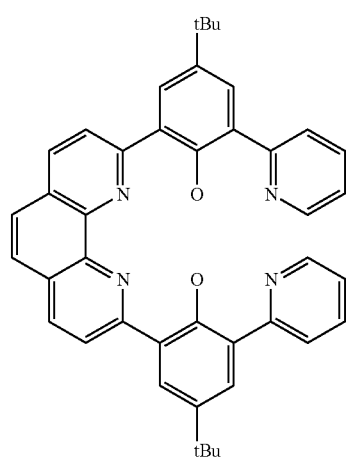
(II)
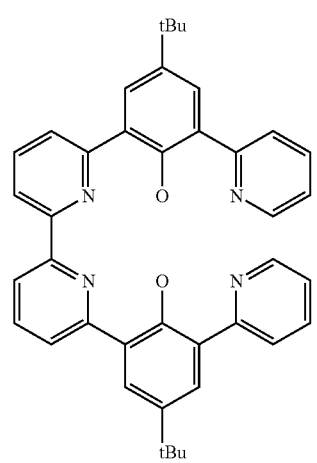
(III)
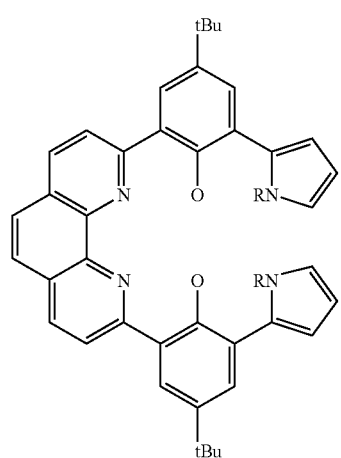
(IV)
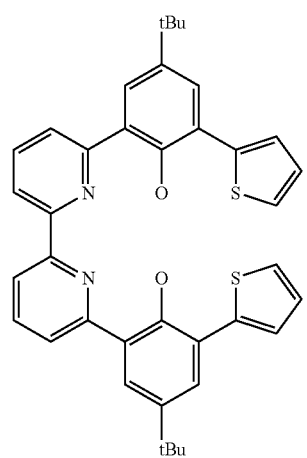
(V)
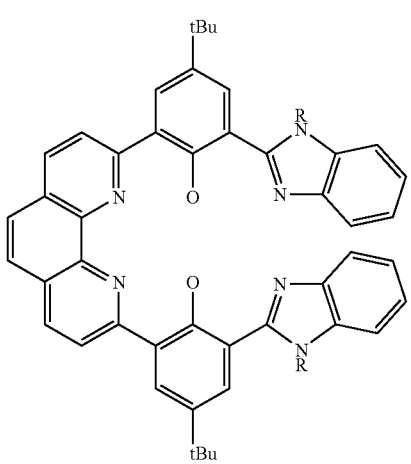
(VI)
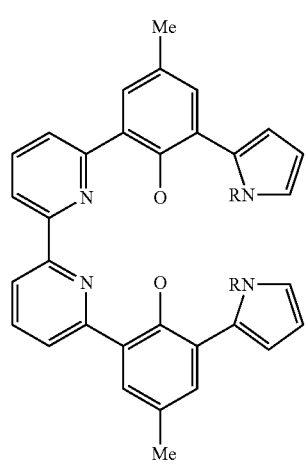

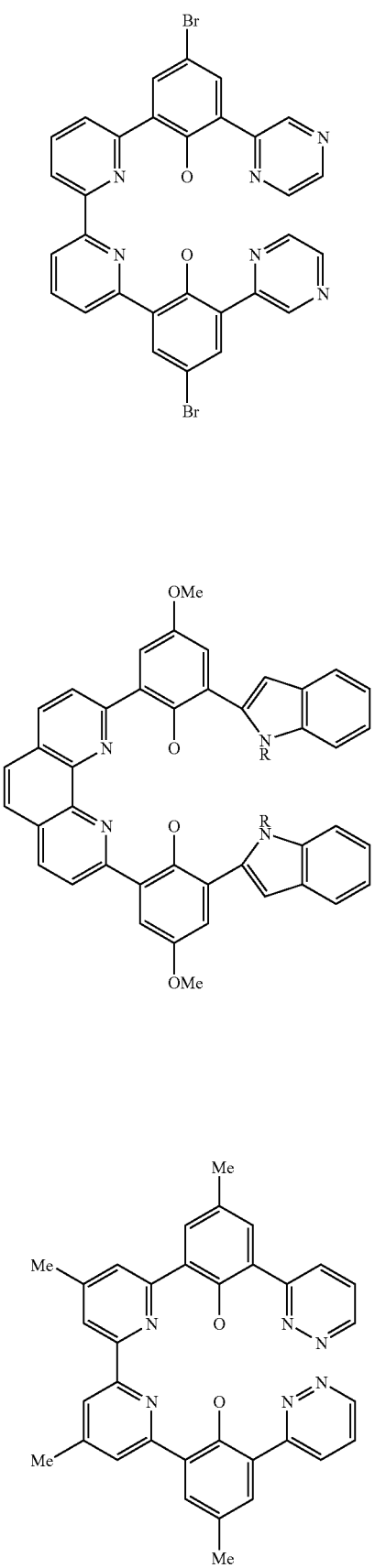
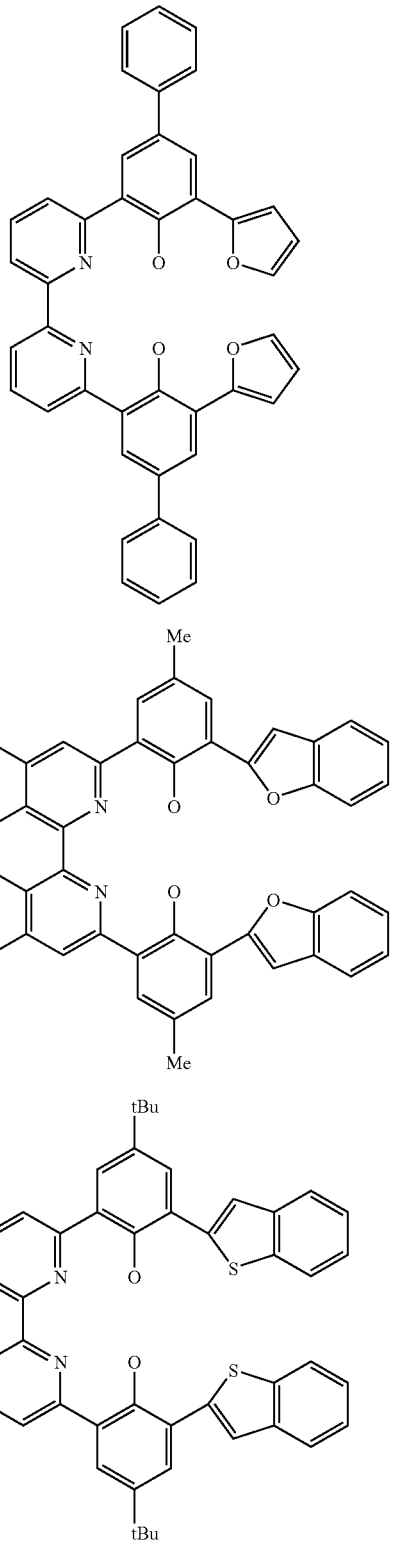
R described in the structure structure (III), (V), (VI) or (VIII) represents a hydrogen atom or a hydrocarbon group having 1 to 30 carbon atoms.
In the structures (I) to (XII), an electric charge is omitted.
X in each of the formulae (1) and (2) represents a neutral molecule or a counter ion that electrically neutralizes the metal complex. Examples of the neutral molecule include a molecule that solvates to form a solvated salt and a ligand except the cyclic ligand in each of the above formulae (1) and (2). Specific examples of the neutral molecule include water, methanol, ethanol, n-propanol, isopropyl alcohol, 2-methoxyethanol, 1,1-dimethyl ethanol, ethylene glycol, N,N'-dimethyl formamide, N,N'-dimethyl acetamide, N-methyl-2-pyrrolidone, dimethyl sulfoxide, acetone, chloroform, acetonitrile, benzonitrile, triethyl amine, pyridine, pyrazine, diazabicyclo[2,2,2]octane, 4,4'-bipyridine, tetrahydrofuran, diethyl ether, dimethoxy ethane, methylethyl ether, and 1,4-dioxane, and preferably water, methanol, ethanol, isopropyl alcohol, ethylene glycol, N,N'-dimethyl formamide, N,N'-dimethyl acetamide, N-methyl-2-pyrrolidone, chloroform, acetonitrile, benzonitrile, triethyl amine, pyridine, pyrazine, diazabicyclo[2,2,2]octane, 4,4'-bipyridine, tetrahydrofuran, dimethoxy ethane, and 1,4-dioxane.

In addition, when X represents an ion, because the transition metal atom and typical metal atom generally have a positive charge, a negative ion which neutralizes the atom electrically is selected and X represents a fluorine ion, a chlorine ion, a bromine ion, an iodine ion, a sulfide ion, an oxide ion, a hydroxide ion, a hydride ion, a sulfite ion, a phosphate ion, a cyanide ion, an acetate ion, a carbonate ion, a sulfate ion, a nitrate ion, a hydrogen carbonate ion, a trifluoroacetate ion, a 2-ethylhexanoate ion, a thiocyanide ion, a trifluoromethane sulfonate ion, an acetyl acetonate, a tetrafluoroborate ion, a hexafluorophosphate ion, and a tetraphenyl borate ion, and preferably a chloride ion, a bromide ion, an iodide ion, an oxide ion, a hydroxide ion, a hydride ion, a phosphate ion, a cyanide ion, an acetate ion, a carbonate ion, a sulfate ion, a nitrate ion, a 2-ethylhexanoate ion, an acetyl acetonate, and a tetraphenyl borate ion.

In addition, when a plurality of X's are present, the X's may be the same as or different from each other, or a neutral molecule and an ion may be coexistent with each other.

To be specific, the metal complex represented by the formula (2) is preferably obtained by combining any one of the ligand structures (I) to (XII) shown above and the specific examples of M and X described above and a particularly preferable metal complex is a metal complex obtained by combining any one of the ligand structures (I) to (IV) shown above, the transition metal atom M belonging to Period 4, and an acetate ion, a chloride ion, a nitrate ion, and a 2-ethylhexanoate ion.

A polymer having a residue of the metal complex represented by formula (1) or (2) means to a polymer having a group comprising an atomic group obtained by removing a part or all of the hydrogen atoms (one hydrogen atom in ordinary cases) in the metal complex represented by the formula (1) or (2), and the polymer to be used in this case is not particularly limited and examples of the polymer include a conductive polymer, a dendrimer, a natural polymer, a solid polymer electrolyte, polyethylene, polyethylene glycol, and polypropylene. Of those, the conductive polymer or the solid polymer electrolyte is particularly preferred. The term "conductive polymer" is a collective term for polymer substances each showing metallic or semi-metallic conductivity (Iwanami Physical and Chemical Science Dictionary, fifth edition: issued in 1988). Examples of the conductive polymer include: polyacetylene and a derivative of polyacetylene, polyparaphenylene and a derivative of polyparaphenylene, polyparaphenylene vinylene and a derivative of polyparaphenylene vinylene, polyaniline and a derivative of polyaniline, polythiophene and a derivative of polythiophene, polypyrrole and a derivative of polypyrrole, polyfluorene and a derivative of polyfluorene, polyfluorene and a derivative of polyfluorene, polycarbazole and a derivative of polycarbazole, and polyindole and a derivative of polyindole described in "Conductive Polymer" (written by Shinichi Yoshimura, KYORITSU SHUPPAN CO., LTD) and "New Applications of Conducting Polymers" (edited by Yukio Kobayashi, CMC Publishing CO., LTD.); and copolymers of the conductive polymers.

Examples of the solid polymer electrolyte include polymers obtained by sulfonating perfluorosulfonic acid, polyether ether ketone, polyimide, polyphenylene, polyarylene, and polyarylene ether sulfone.

A polymer having the residue of the metal complex represented by formula (1) or (2) as a repeating unit means to a polymer having the group comprising an atomic group obtained by removing a part or all of the hydrogen atoms (two hydrogen atoms in ordinary cases) in the metal complex represented by formula (1) or (2) as a repeating unit, and the polymer is produced by, for example, polymerizing a bifunctional monomer containing a macrocyclic ligand.

Next, a method of synthesizing the metal complex represented by each of the formulae (1) and (2) will be described.

The metal complex represented by each of the formulae (1) and (2) can be obtained by: synthesizing the ligand organochemically; and mixing the ligand and a reaction agent that provides the metal atom M (hereinafter referred to as "metal-providing agent") in a reaction solvent. Here, the metal-providing agent is a metal salt comprising a combination of the metal atom M and the counter ion X described above. Specific preferable examples of the metal atom M include manganese, iron, cobalt, nickel, and copper, and specific preferable examples of the counter ion X include an acetate ion, a chloride ion, a nitrate ion, and a 2-ethylhexanoate ion; a metal salt comprising a combination of the metal atom M and the counter ion X is preferable.

As described in a non-patent document "Tetrahedron., 1999, 55, 8377", the ligand can be synthesized by: performing an addition reaction of an organometallic reactant to an aromatic heterocyclic compound and an oxidation followed by a halogenation reaction; and further by a cross-coupling reaction with a transition metal catalyst.

Alternatively, the ligand can be synthesized by performing a multistage cross-coupling reaction using a halogenated aromatic heterocyclic compound.

As described above, the metal complex of the present invention can be obtained by mixing the ligand and the metal-providing agent in the presence of a appropriate reaction solvent. Specific examples of the reaction solvent include water, acetic acid, oxalic acid, ammonia water, methanol, ethanol, n-propanol, isopropyl alcohol, 2-methoxyethanol, 1-butanol, 1,1-dimethylethanol, ethylene glycol, diethyl ether, 1,2-dimethoxyethane, methylethyl ether, 1,4-dioxane, tetrahydrofuran, benzene, toluene, xylene, mesitylene, durene, decalin, dichloromethane, chloroform, carbon tetrachloride, chlorobenzene, 1,2-dichlorobenzene, N,N'-dimethylformamide, N,N'-dimethyl acetamide, N-methyl-2-pyrrolidone, dimethylsulfoxide, acetone, acetonitrile, benzonitrile, triethylamine, and pyridine. A reaction solvent obtained by mixing two or more kinds of them may be used and a solvent which can dissolve a ligand and a metal-providing agent is preferred. The reaction can be performed at a temperature of generally −10 to 200° C., preferably 0 to 150° C., or particularly preferably 0 to 100° C. for a time period of generally 1 minute to 1 week, preferably 5 minutes to 24 hours, or particularly preferably 1 hour to 12 hours. It should be noted that the reaction temperature and the reaction time can also be appropriately optimized depending on the kinds of the ligand and the metal-providing agent.

An optimum method selected from a known recrystallization method, a known redeposit method, and a known chromatography method can be appropriately employed as a method involving isolating the produced metal complex from the reaction solution after the reaction and purifying the metal complex, and two or more of these methods may be employed in combination.

It should be noted that the produced metal complex may precipitate depending on the kind of the reaction solvent; the precipitated metal complex can be isolated and purified by separating the metal complex by a solid-liquid separation method such as filtration and subjecting the separated product to a washing operation and a drying operation as required.

Since the basic structures of the metal complexes represented by the formulae (1) and (2) are each aromatic, each of the complexes has high heat resistance and high acid resistance, and hence maintains its structure stably even at high temperatures or even in the presence of a strong acid. Accordingly, each of the complexes is expected to exert a catalytic action related to the two metal sites.

The metal complexes are particularly suitable for use as, for example, redox catalysts, and specific examples of the applications of the metal complexes include: decomposition catalysts for hydrogen peroxide; oxidation polymerization catalysts for aromatic compounds; catalysts for purifying an exhaust gas and waste water; redox catalyst layers for dye sensitization solar cells; carbon dioxide reduction catalysts; catalysts for the production of reformed hydrogen; and oxygen sensors. In addition, the metal complexes can be used as organic semiconductor materials such as organic EL materials, organic transistors, and dye sensitization solar cells by taking advantage of the fact that each of the metal complexes has an expanded conjugation.

The metal complex of the present invention is excellent in stability (such as heat resistance and acid resistance), and is useful as, for example, a redox reaction catalyst. That is the metal complex is inhibited from decreasing in its catalystic activity and can serve as a catalyst for a wide vaiiety of applications and therefore the metal complex is industrially useful.

The present invention will be described in more detail based on the following examples, but the invention is not intended to be limited thereto. In EXAMPLE, Me, Et, and Ac represent methyl, ethyl, and acetyl, respectively.

EXAMPLES

Example 1

Synthesis of Metal Complex (A)

Metal complex (A) was synthesized by mixing a ligand and 2-methoxyethanol solution containing cobalt acetate tetrahydrate and by causing them to react with each other in accordance with the following reaction formula. The following ligand as a raw material for the complex was synthesized on the basis of Tetrahedron., 1999, 55, 8377.

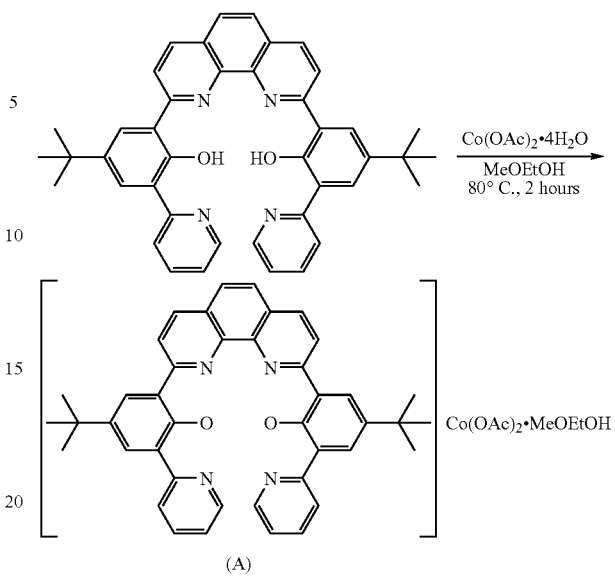

(A)

First, under a nitrogen atmosphere, 1.388 g of the ligand and 200 mL of 2-methoxyethanol solution containing 1.245 g of cobalt acetate tetrahydrate were loaded into a 500-mL egg plant flask, and the mixture was stirred for 2 hours while being heated at 60° C., whereby a brown solid was produced. The solid was taken by filtration, and was then washed with 20 mL of 2-methoxyethanol and dried, whereby Metal Complex (A) was obtained (yield 1.532 g). The infrared ray (IR) absorption spectrum of the obtained Metal Complex (A) is shown in FIG. 1.

Elementary Analysis Value (%):

Calculated Value (Calcd for $C_{49}H_{50}Co_2N_4O_8$); C, 62.56; H, 5.36; N, 5.96; Co, 12.53

Actual Measurement Value: C, 62.12; H, 5.07; N, 6.03; Co, 12.74

ESI-MS $[M-OAc]^+$: 805.0

Example 2

Synthesis of Metal Complex (B)

Metal complex (B) was synthesized by mixing a ligand and ethanol solution containing cobalt acetate tetrahydrate and by causing them to react with each other in accordance with the following reaction formula. The following ligand as a raw material for the complex was synthesized on the basis of Tetrahedron., 1999, 55, 8377.

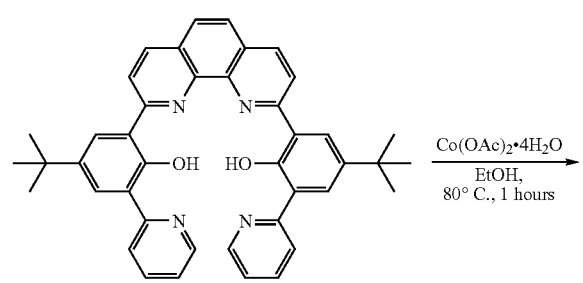

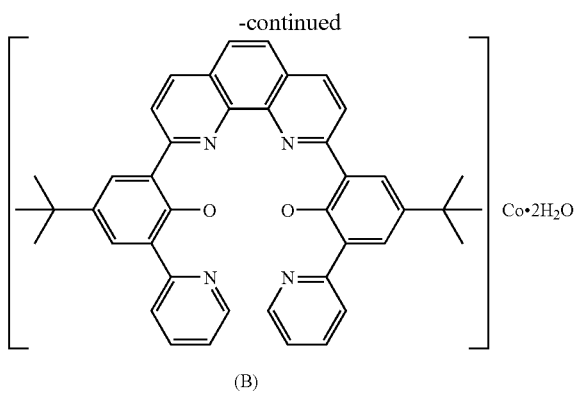

(B)

First, under a nitrogen atmosphere, 0.315 g of the ligand and 50 mL of ethanol solution containing 0.124 g of cobalt acetate tetrahydrate were loaded into a 100-mL egg plant flask, and the mixture was stirred for 1 hour while being heated at 80° C. The produced brown deposit was taken by filtration, washed with ethanol, and dried in a vacuum, whereby Metal Complex (B) was obtained (yield 0.270 g).

Elementary Analysis Value (%):
Calculated Value (Calcd for $C_{42}H_{40}CoN_4O_4$); C, 69.70; H, 5.57; N, 7.74
Actual Measurement Value: C, 70.01; H, 5.80; N, 7.56
ESI-MS [M•]$^+$: 687.1

Example 3

Synthesis of Metal Complex (C)

Metal complex (C) was synthesized by mixing ethanol solution containing a ligand and methanol solution containing ferrous acetate and by causing them to react with each other in accordance with the following reaction formula. The following ligand as a raw material for the complex was synthesized on the basis of Tetrahedron., 1999, 55, 8377.

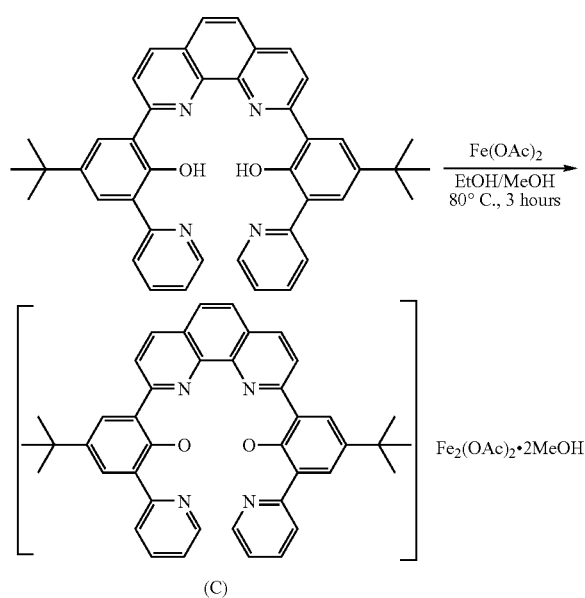

(C)

First, under a nitrogen atmosphere, 10 mL of ethanol solution containing 0.126 g of the ligand and 5 mL of methanol solution containing 0.078 g of ferrous acetate were loaded into a 50-mL egg plant flask, and the mixture was stirred for 3 hours while being heated at 80° C., whereby a brown solid was precipitated. The solid was taken by filtration, and was then washed with methanol and dried, whereby Metal Complex (C) was obtained (yield 0.075 g).

Elementary Analysis Value (%):
Calculated Value (Calcd for $C_{48}H_{50}Fe_2N_4O_8$); C, 62.49; H, 5.46; N, 6.07
Actual Measurement Value: C, 59.93; H, 5.29; N, 5.70

Example 4

Synthesis of Metal Complex (D)

Metal Complex (D) was synthesized by mixing chloroform solution containing a ligand and ethanol solution containing manganous chloride tetrahydrate and by causing them to react with each other in accordance with the following reaction formula. The following ligand as a raw material for the complex was synthesized on the basis of Tetrahedron., 1999, 55, 8377.

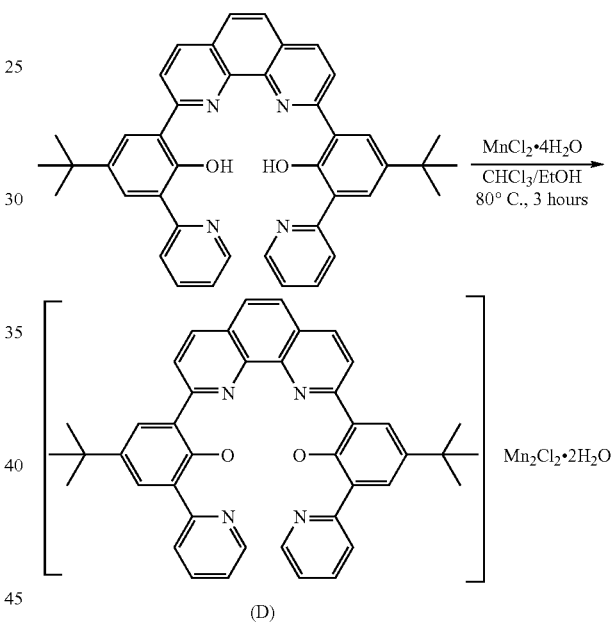

(D)

First, under a nitrogen atmosphere, 2 mL of chloroform solution containing 0.126 g of the ligand and 6 mL of ethanol solution containing 0.089 g of manganous chloride tetrahydrate were loaded into a 25-mL egg plant flask, and the mixture was stirred for 3 hours while being heated at 80° C., whereby a yellow solid was precipitated. The solid was taken by filtration, and was then washed with chloroform and ethanol, and dried, whereby Metal Complex (D) was obtained (yield 0.092 g).

Elementary Analysis Value (%):
Calculated Value (Calcd for $C_{42}H_{40}Mn_2N_4O_4$); C, 59.66; H, 4.77; N, 6.63
Actual Measurement Value: C, 58.26; H, 4.58; N, 6.33
FD-MS [M•]$^+$: 808.0

Example 5

Synthesis of Metal Complex (E)

Metal Complex (E) was synthesized by mixing ethanol solution containing a ligand and methanol solution containing manganese acetate tetrahydrate and by causing them to react with each other in accordance with the following reaction formula. The following ligand as a raw material for the complex was synthesized on the basis of Tetrahedron., 1999, 55, 8377.

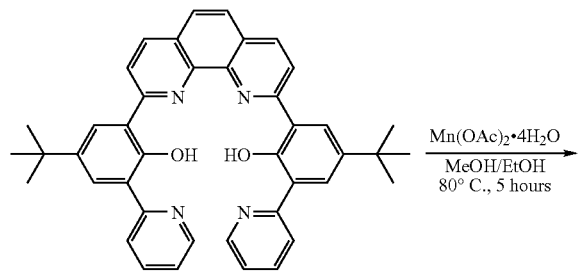

First, under a nitrogen atmosphere, 10 mL of ethanol solution containing 0.100 g of the ligand and 2.5 mL of methanol solution containing 0.042 g of manganese acetate tetrahydrate were loaded into a 25-mL egg plant flask, and the mixture was stirred for 5 hours while being heated at 80° C. The resultant solution was dropped to 20 mL of saturated aqueous solution of ammonium acetate, and the mixture was stirred for 1 hour. The precipitated solid was taken by filtration and dried, whereby Metal Complex (E) was obtained (yield 0.029 g).

ESI-MS [M•]$^+$: 683.1

Example 6

Synthesis of Metal Complex (F)

Metal Complex (F) was synthesized by mixing a ligand and chloroform solution containing cobalt 2-ethylhexanoate and by causing them to react with each other in accordance with the following reaction formula. The following ligand as a raw material for the complex was synthesized on the basis of Tetrahedron., 1999, 55, 8377.

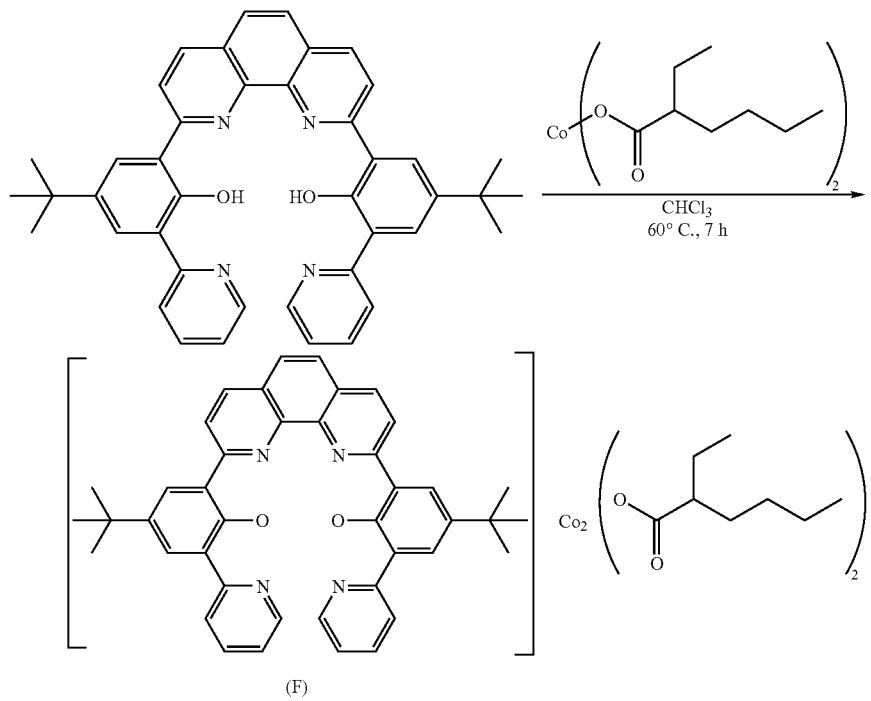

(F)

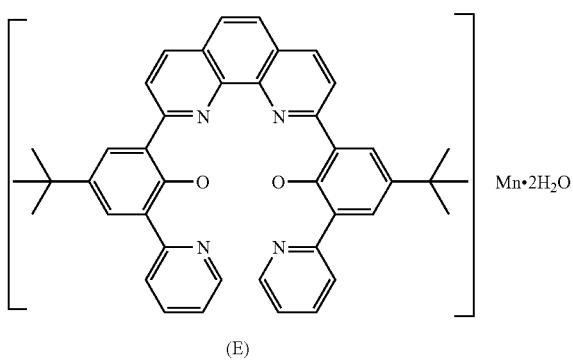

(E)

First, under a nitrogen atmosphere, 0.077 g of the ligand and 5 mL of chloroform solution containing 0.239 g of cobalt 2-ethylhexanoate (65 wt % mineral oil solution) were loaded into a 25-mL egg plant flask, and the mixture was stirred for 9 hours while being heated at 60° C. The solution was dropped to an Erlenmeyer flask containing 50 mL of diethyl ether. The precipitated solid was taken by filtration, washed with diethyl ether, and dried, whereby Metal Complex (F) was obtained (yield 0.146 g).

ESI-MS [M•]$^+$: 1032.2

Elementary Analysis Value (%):

Calculated Value (Calcd for $C_{58}H_{66}Co_2N_4O_6$); C, 67.43; H, 6.44; N, 5.42

Actual Measurement Value: C, 66.97; H, 6.21; N, 5.27

Example 7

Synthesis of Metal Complex (G)

Metal Complex (G) was synthesized by mixing a ligand and ethanol solution containing nickel acetate tetrahydrate and by causing them to react with each other in accordance with the following reaction formula. The following ligand as a raw material for the complex was synthesized on the basis of Tetrahedron., 1999, 55, 8377.

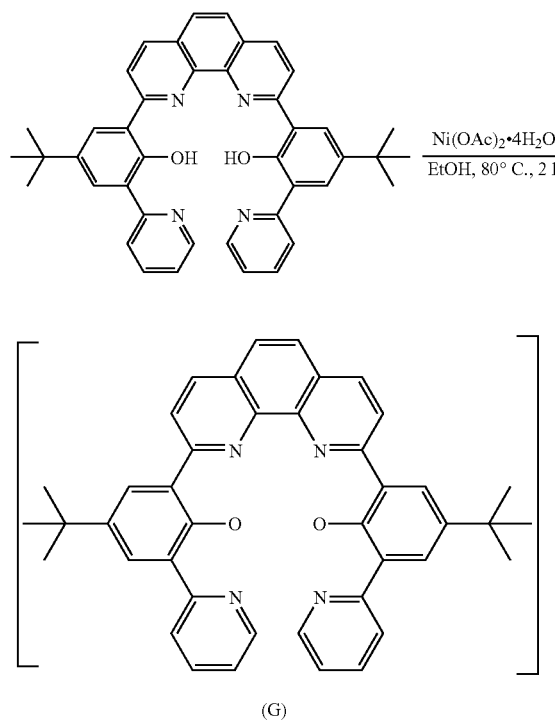

First, under a nitrogen atmosphere, 0.250 g of the ligand and 30 mL of ethanol solution containing 0.100 g of nickel acetate tetrahydrate were loaded into a 50-mL egg plant flask, and the mixture was stirred for 2 hours while being heated at 80° C. The produced orange deposit was taken by filtration, washed with ethanol, and dried in a vacuum, whereby Metal Complex (G) was obtained (yield 0.242 g).

Elementary Analysis Value (%):

Calcd for $C_{42}H_{36}N_4NiO_2$; C, 73.38; H, 5.28; N, 8.15. Found: C, 72.42; H, 5.27; N, 7.96.

ESI-MS [M•]$^+$: 687.1

Example 8

Synthesis of Metal Complex (H)

Metal Complex (H) was synthesized by mixing a ligand and ethanol solution containing cupric acetate monohydrate and by causing them to react with each other in accordance with the following reaction formula. The following ligand as a raw material for the complex was synthesized on the basis of Tetrahedron., 1999, 55, 8377.

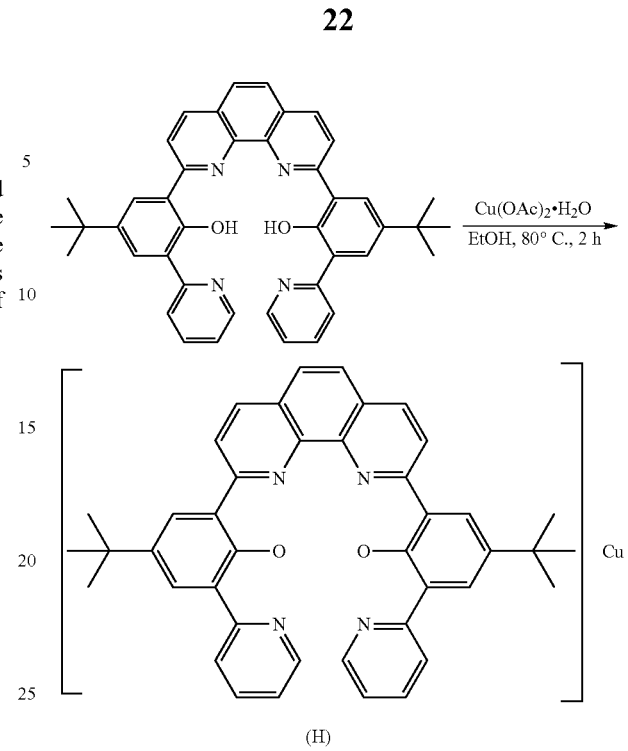

First, under a nitrogen atmosphere, 0.315 g of the ligand and 30 mL of ethanol solution containing 0.100 g of cupric acetate monohydrate were loaded into a 50-mL egg plant flask, and the mixture was stirred for 2 hours while being heated at 80° C. The produced ocher deposit was taken by filtration, washed with ethanol, and dried in a vacuum, whereby Metal Complex (H) was obtained (yield 0.250 g).

Elementary Analysis Value (%):

Calcd for $C_{42}H_{36}CuN_4O_2$; C, 72.87; H, 5.24; N, 8.09. Found: C, 72.22; H, 5.37; N, 7.77

ESI-MS [M•]$^+$: 692.1

Example 9

Synthesis of Metal Complex (I)

Metal Complex (I) was synthesized by mixing a ligand and ethanol solution containing ferrous acetate and by causing them to react with each other in accordance with the following reaction formula. The following ligand as a raw material for the complex was synthesized on the basis of Tetrahedron., 1999, 55, 8377.

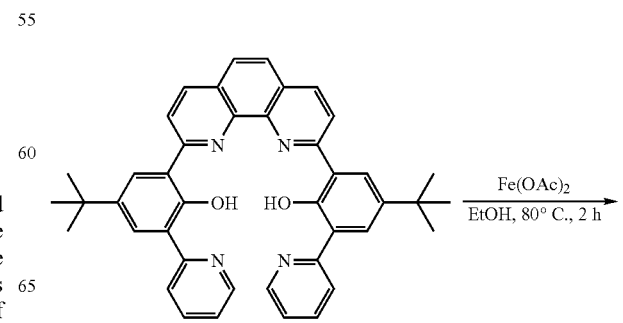

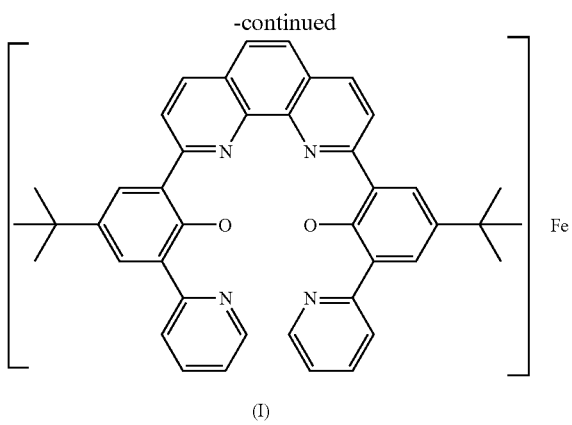

(I)

First, under a nitrogen atmosphere, 0.440 g of the ligand and 30 mL of ethanol solution containing 0.120 g of ferrous acetate were loaded into a 50-mL egg plant flask, and the mixture was stirred for 2 hours while being heated at 80° C. The produced orange deposit was taken by filtration, washed with ethanol, and dried in a vacuum, whereby Metal Complex (I) was obtained (yield 0.380 g).

Elementary Analysis Value (%):
Calcd for $C_{42}H_{36}FeN_4O_2$; C, 73.68; H, 5.30; N, 8.18.
Found: C, 72.20; H, 5.42; N, 7.85.
ESI-MS $[M\bullet]^+$: 684.0

Example 10

Synthesis of Metal Complex (J)

Metal Complex (J) was synthesized by mixing a ligand and ethanol solution containing nickel acetate and by causing them to react with each other in accordance with the following reaction formula. The following ligand as a raw material for the complex was synthesized on the basis of Tetrahedron., 1999, 55, 8377.

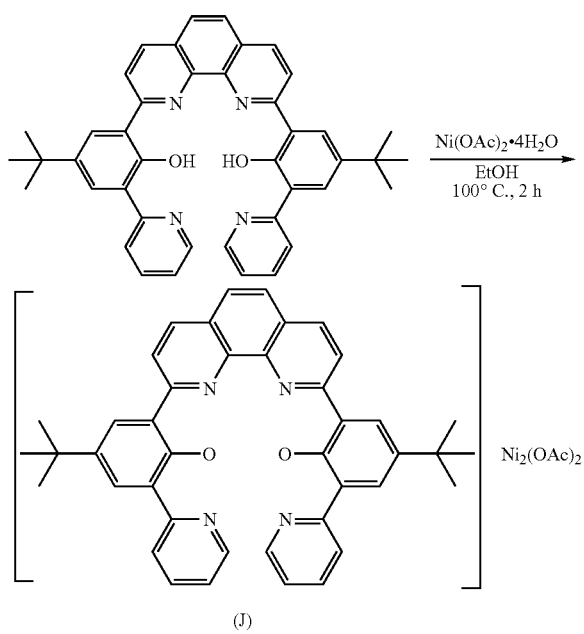

(J)

First, under a nitrogen atmosphere, 0.200 g of the ligand and 30 mL of ethanol solution containing 0.250 g of nickel acetate tetrahydrate were loaded into a 50-mL egg plant flask, and the mixture was stirred for 2 hours while being heated at 100° C., whereby an orange solid was precipitated. The solid was taken by filtration, washed with ethanol and diethyl ether, and dried, whereby Metal Complex (J) was obtained (yield 0.276 g).

Elementary Analysis Value (%):
Calculated Value (Calcd for $C_{46}H_{42}N_4Ni_2O_6$): C, 63.93; H, 4.90; N, 6.07
Actual Measurement Value: C, 63.22; H, 5.02; N, 6.43

Example 11

Synthesis of Metal Complex (K)

Metal Complex (K) was synthesized by mixing chloroform solution containing a ligand and methanol solution containing cobalt nitrate hexahydrate and by causing them to react with each other in accordance with the following reaction formula. The following ligand as a raw material for the complex was synthesized on the basis of Tetrahedron., 1999, 55, 8377.

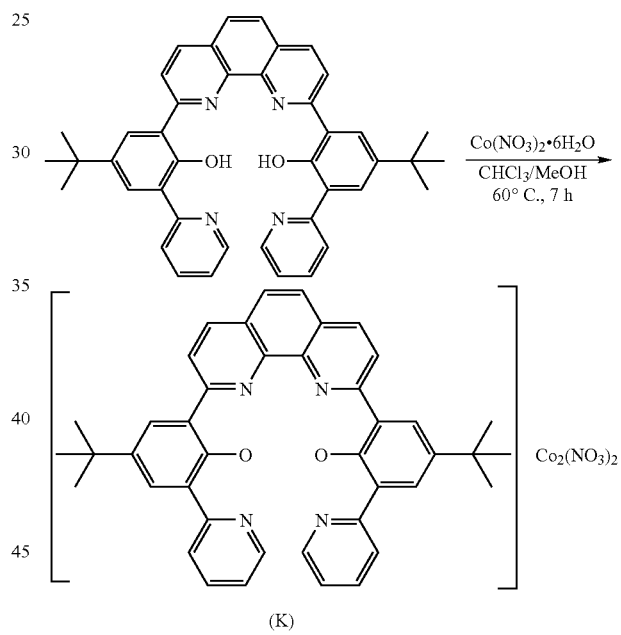

(K)

First, under a nitrogen atmosphere, a mixed solution of 2 mL of chloroform solution and 5 mL of methanol containing 0.096 g of the ligand and 0.082 g of cobalt nitrate hexahydrate were loaded into a 100-mL egg plant flask, and the mixture was stirred for 7 hours while being heated at 60° C., whereby a yellow solid was produced. The solid was taken by filtration, and was then washed with methanol and dried, whereby Metal Complex (K) was obtained (yield 0.036 g).

ESI-MS $[M-NO_3]^+$: 808.0

Example 12

Synthesis of Metal Complex (L)

Metal Complex (L) was synthesized by mixing chloroform/ethanol mixed solution containing the Metal Complex (B) and ethanol solution containing copper chloride and by causing them to react with each other in accordance with the following reaction formula.

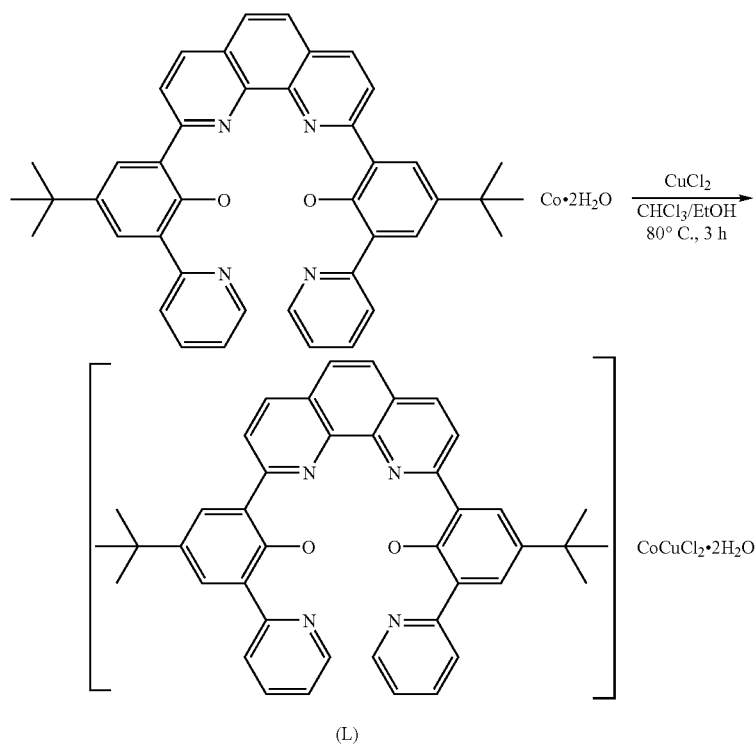

(L)

Under a nitrogen atmosphere, a mixed solution of 1 mL of chloroform and 2 mL of ethanol containing 0.066 g of Metal Complex (B) was charged into a 25-mL egg plant flask, and 4 mL of ethanol containing 0.013 of copper(II) chloride was dropped to the flask. The solution was stirred for 3 hours while being heated at 80° C. The precipitated solid was taken by filtration, and was then washed with methanol and dried, whereby Metal Complex (L) was obtained (yield 0.054 g).

ESI-MS [M-Cl]$^+$: 787.0

Example 13
Synthesis of Metal Complex (M)

Metal Complex (M) was synthesized by mixing a ligand and ethanol solution containing cobalt acetate tetrahydrate and by causing them to react with each other in accordance with the following reaction formula. The following ligand as a raw material for the complex was synthesized on the basis of Tetrahedron., 1999, 55, 8377.

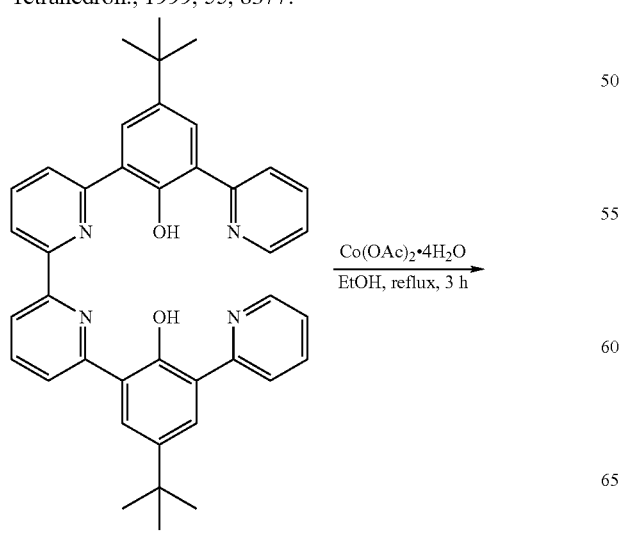

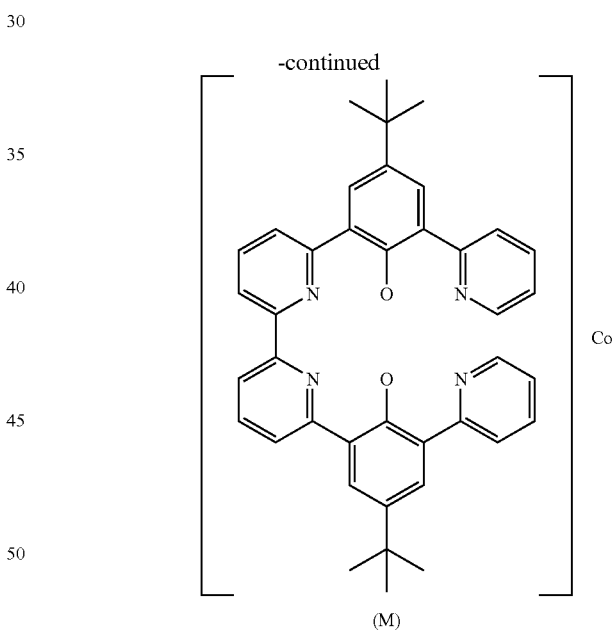

(M)

Under a nitrogen atmosphere, 0.303 g of the ligand and solution of 0.125 g of cobalt acetate tetrahydrate were loaded into a 100-mL two-necked flask, and 50 mL of ethanol was added thereto. The solution was refluxed for 3 hours, whereby an ocher solid was produced. The deposit was taken by filtration and dried, whereby Metal Complex (M) was obtained (yield 0.242 g).

ESI-MS [M+H]$^+$: 664.2

Figure 2:
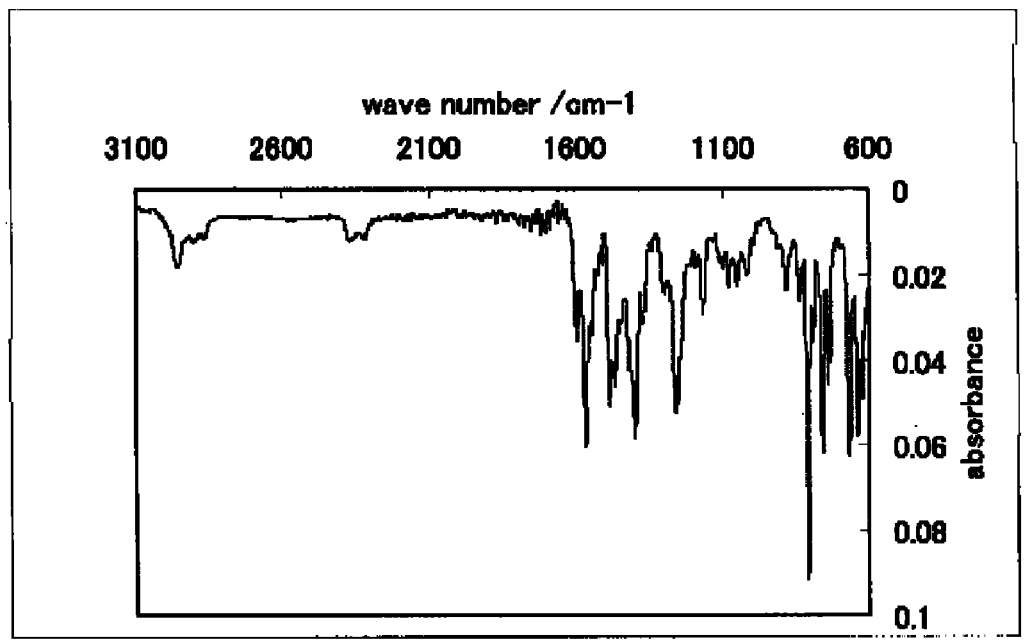
FIG. 2 shows an IR absorption spectrum of Metal Complex (M).

The infrared ray (IR) absorption spectrum of the obtained Metal Complex (M) is shown in FIG. 2.

27

Example 14

Synthesis of Metal Complex (N)

Metal Complex (N) was synthesized by mixing a ligand and ethanol solution containing cobalt acetate tetrahydrate and by causing them to react with each other in accordance with the following reaction formula. The following ligand as a raw material for the complex was synthesized on the basis of Tetrahedron., 1999, 55, 8377.

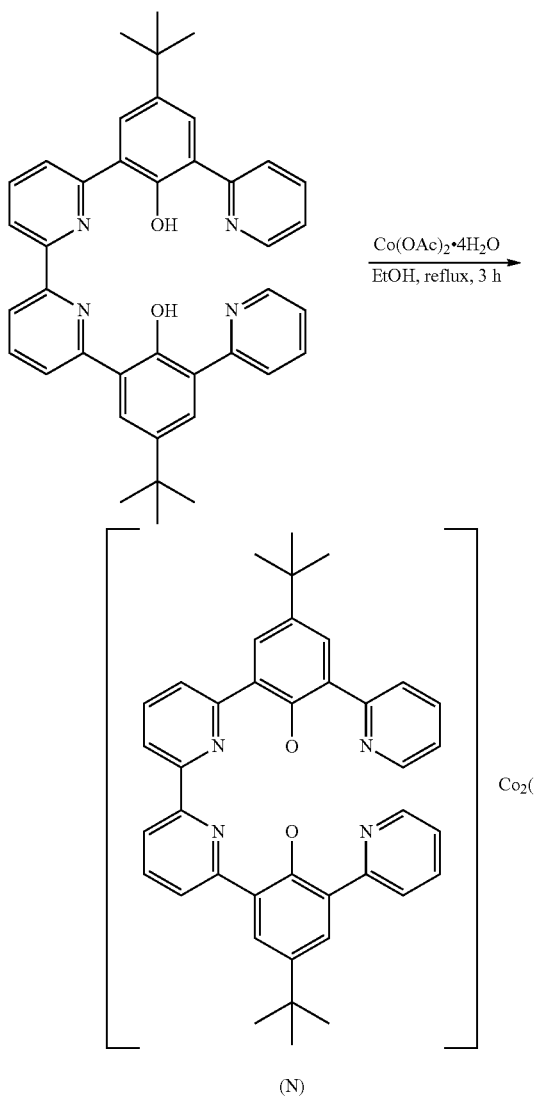

(N)

Under a nitrogen atmosphere, 0.303 g of the ligand and solution of 0.324 g of cobalt acetate tetrahydrate were loaded into a 100-mL two-necked flask, and mixed solution of 20 mL of ethanol and 20 mL of chloroform was added thereto. The solution was refluxed for 3 hours, whereby an ocher solid was produced. The deposit was taken by filtration and dried, whereby Metal Complex (N) was obtained (yield 0.133 g).

ESI-MS [M-OAc]$^+$: 781.0

Figure 3:
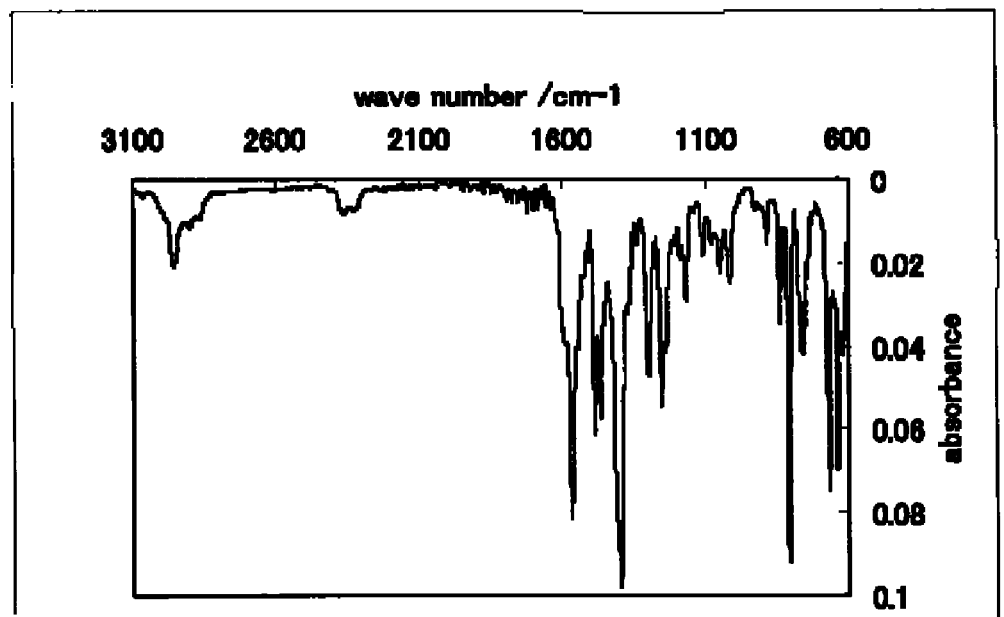
FIG. 3 shows an IR absorption spectrum of Metal Complex (N).

The infrared ray (IR) absorption spectrum of the obtained Metal Complex (N) is shown in FIG. 3.

Metal Complex (Q) was synthesized via Compound (O) and Ligand (P) in accordance with the following reaction formula.

28

Synthesis Example 1

Synthesis of Compound (O)

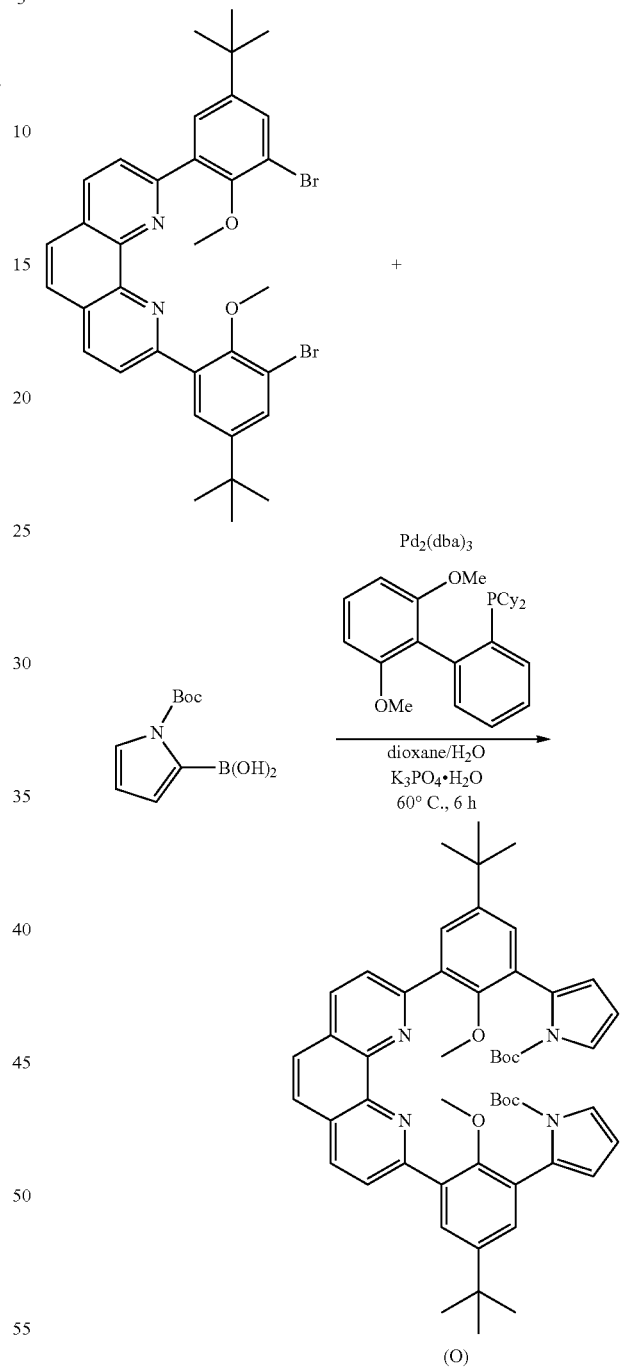

(O)

Under an argon atmosphere, 3.945 g of 2,9-di(3'-bromo-5'-tert-butyl-2'-methoxyphenyl)-1,10-phenanthroline, 3.165 g of 1-N-Boc-pyrrole-2-boronic acid, 0.138 g of tris(benzylideneacetone)dipalladium, 0.247 g of 2-dicyclohexylphosphino-2',6'-dimethoxybiphenyl, and 5.527 g of potassium phosphate were dissolved in mixed solvent of 200 mL of dioxane and 20 mL of water, and the solution was stirred at 60° C. for 6 hours. After the completion of the reaction, the solution was left standing to cool, distilled water and chloroform were added to the solution, and an organic layer was extracted. The resultant organic layer was concentrated, whereby a black residue was obtained. The residue was purified with a silica gel column, whereby Compound (O) was obtained.

$^1$H-NMR (300 MHz, CDCl$_3$) δ 1.34 (s, 18H), 1.37 (s, 18H), 3.30 (s, 6H), 6.21 (m, 2H), 6.27 (m, 2H), 7.37 (m, 2H), 7.41 (s, 2H), 7.82 (s, 2H), 8.00 (s, 2H), 8.19 (d, J=8.6 Hz, 2H), 8.27 (d, J=8.6 Hz, 2H)

Synthesis Example 2

Synthesis of Ligand (P)

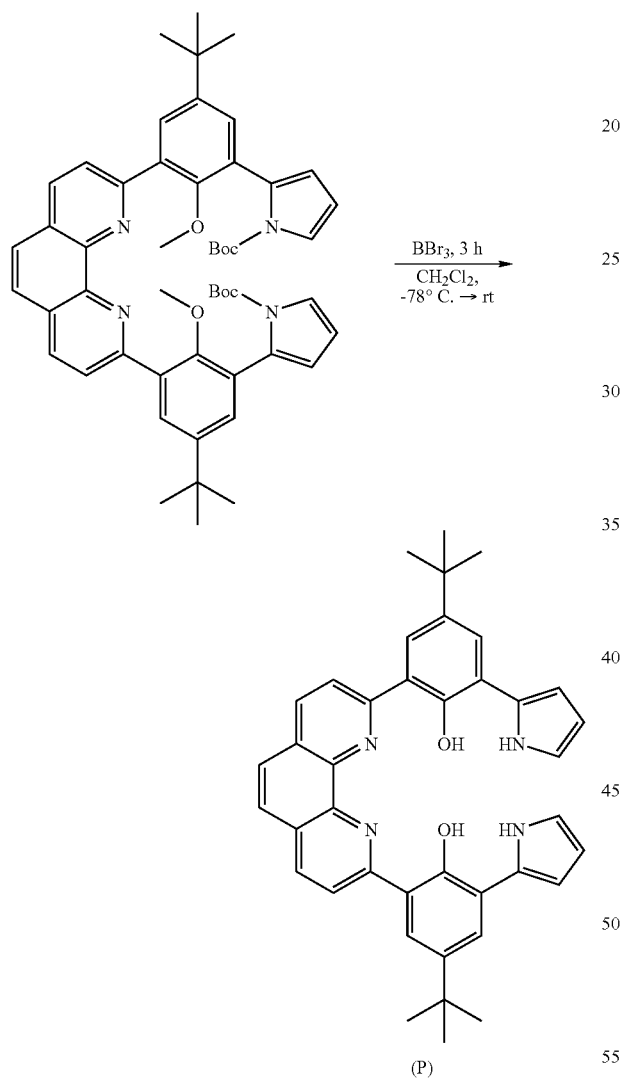

(P)

Under a nitrogen atmosphere, 0.904 g of Compound (O) was dissolved in 10 mL of anhydrous dichloromethane. While the dichloromethane solution was cooled to −78° C., 8.8 mL of boron tribromide (1.0-M dichloromethane solution) was slowly dropped to the dichloromethane solution. After the dropping, the mixture was stirred for 10 minutes, and was then left to stand while being stirred so that its temperature might reach room temperature. Three hours after that, the reaction solution was cooled to 0° C., and a saturated aqueous solution of NaHCO$_3$ was added to the solution. After that, an organic layer was extracted by adding chloroform to the mixture, and was then concentrated. The obtained brown residue was purified with a silica gel column, whereby Ligand (P) was obtained.

$^1$H-NMR (300 MHz, CDCl$_3$) δ 1.40 (s, 18H), 6.25 (m, 2H), 6.44 (m, 2H), 6.74 (m, 2H), 7.84 (s, 2H), 7.89 (s, 2H), 7.92 (s, 2H), 8.35 (d, J=8.4 Hz, 2H), 8.46 (d, J=8.4 Hz, 2H), 10.61 (s, 2H), 15.88 (s, 2H).

Example 15

Synthesis of Metal Complex (Q)

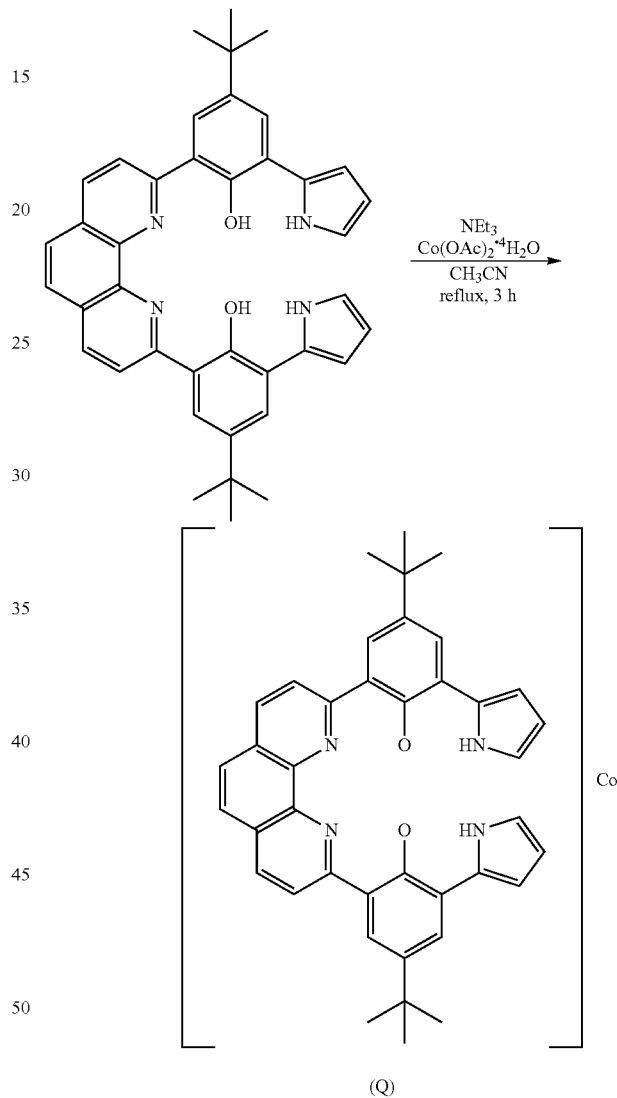

(Q)

Under a nitrogen atmosphere, 20 mL of acetonitrile solution containing 0.100 g of Ligand (P) and 0.040 g of cobalt acetate tetrahydrate, the solution being deaerated with Ar, were loaded into a 100-mL two-necked flask, and the mixture was stirred at room temperature. To the solution, 45 µl of triethylamine was dropped, and the mixture was refluxed for 3 hours. The solution was concentrated and cooled, and then the resultant solid was taken by filtration with a membrane filter and dried, whereby Metal Complex (Q) was obtained (yield 0.098 g).

ESI-MS [M•]$^+$: 663.1

Metal Complex (T) was synthesized via Compound (R) and Ligand (S) in accordance with the following reaction formula.

Synthesis Example 3

Synthesis of Compound (R)

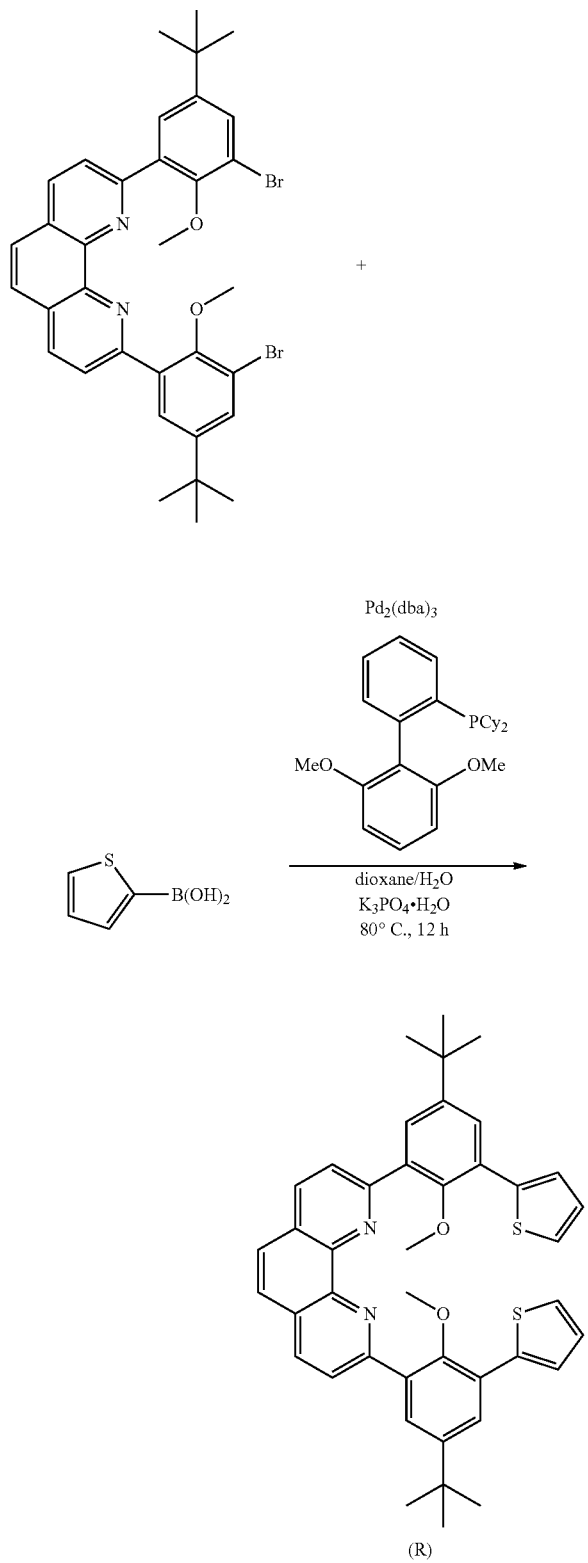

Under an argon atmosphere, 0.662 g of 2,9-di(3'-bromo-5'-tert-butyl-2'-methoxyphenyl)-1,10-phenanthroline, 0.320 g of 2-thienylboronic acid, 0.090 g of tris(benzylideneacetone)dipalladium, 0.160 g of 2-dicyclohexylphosphino-2',6'-dimethoxybiphenyl, and 0.920 g of potassium phosphate were dissolved in a mixed solvent of 30 mL of dioxane and 5 mL of water, and the solution was stirred at 80° C. for 12 hours. After the completion of the reaction, the solution was left standing to cool, distilled water and chloroform were added to the solution, and an organic layer was extracted. The resultant organic layer was concentrated, whereby a black residue was obtained. The residue was purified with a silica gel column, and then the purified product was recrystallized, whereby Compound (R) was obtained.

$^1$H-NMR (300 MHz, CDCl$_3$) δ 1.42 (s, 18H), 3.48 (s, 6H), 7.12 (dd, 2H), 7.38 (d, J=5.0 Hz, 2H), 7.52 (d, J=2.9 Hz, 2H), 7.73 (s, 2H), 7.87 (s, 2H), 7.98 (s, 2H), 8.28 (d, J=8.6 Hz, 2H), 8.30 (d, J=8.6 Hz, 2H).

Synthesis Example 4

Synthesis of Ligand (S)

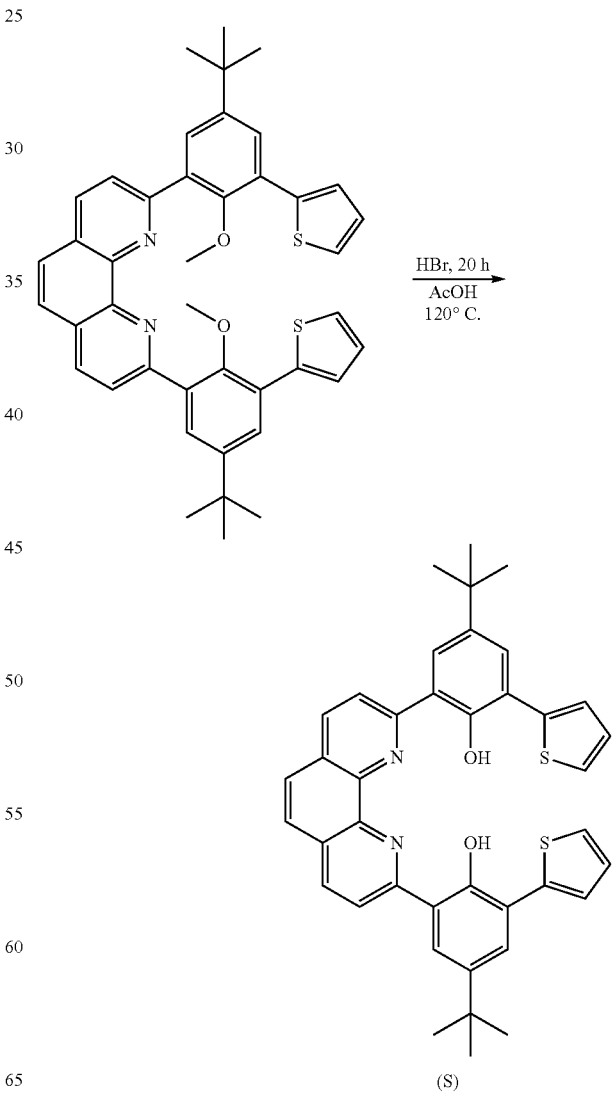

Under a nitrogen atmosphere, 0.134 g of Compound (R) was dissolved in 5 mL of acetic acid. To the solution, 0.337 g of 48% hydrobromic acid was dropped, and the mixture was stirred at 120° C. Twenty hours after that, the reaction solution was cooled to 0° C., and water was added to the solution. After that, an organic layer was extracted by adding chloroform to the mixture, and was then concentrated. The obtained residue was purified with a silica gel column, whereby Ligand (S) was obtained.

$^1$H-NMR (300 MHz, CDCl$_3$) δ 1.40 (s, 18H), 6.25 (m, 2H), 6.44 (m, 2H), 6.74 (m, 2H), 7.84 (s, 2H), 7.89 (s, 2H), 7.92 (s, 2H), 8.35 (d, J=8.4 Hz, 2H), 8.46 (d, J=8.4 Hz, 2H), 10.61 (s, 2H), 15.88 (s, 2H)

Example 16

Synthesis of Metal Complex (T)

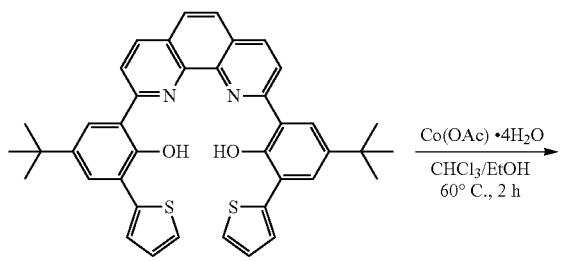

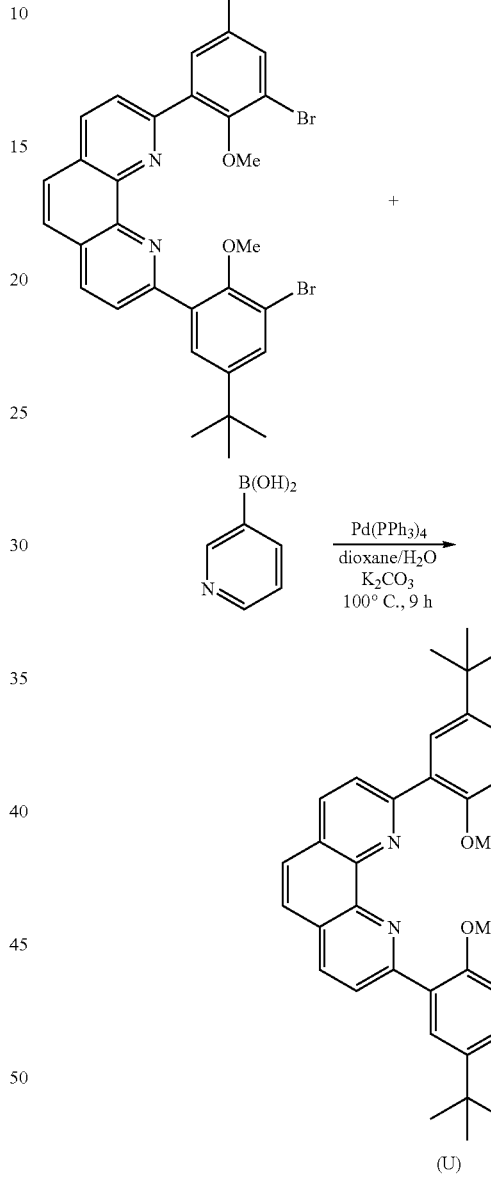

Under a nitrogen atmosphere, 0.062 g of Ligand (S) and mixed solution of 2 mL of chloroform and 6 mL of ethanol containing 0.025 g of cobalt acetate tetrahydrate were loaded into a 25-mL egg plant flask, and the mixture was stirred for 2 hours while being heated at 60° C., whereby a brown solid was produced. The solid was taken by filtration, and was then washed with ethanol and dried, whereby Metal Complex (T) was obtained (yield 0.034 g).

ESI-MS [M•]$^+$: 697.0

Metal Complex (W) was synthesized via Compound (U) and Ligand (V) in accordance with the following reaction formula.

Synthesis Example 5

Synthesis of Compound (U)

Under an argon atmosphere, 0.132 g of 2,9-di(3'-bromo-5'-tert-butyl-2'-methoxyphenyl)-1,10-phenanthroline, 0.061 g of 3-pyridylboronic acid, 0.046 g of tetrakis(triphenylphosphino)palladium, and 0.111 g of potassium carbonate were dissolved in mixed solvent of 5 mL of dioxane and 0.5 mL of water, and the solution was stirred at 100° C. for 9 hours. After the completion of the reaction, the solution was left standing to cool, distilled water and chloroform were added to the solution, and an organic layer was extracted. The resultant organic layer was concentrated, whereby a black residue was obtained. The residue was purified with a silica gel column, whereby Compound (U) was obtained.

Synthesis Example 6

Synthesis of Ligand (V)

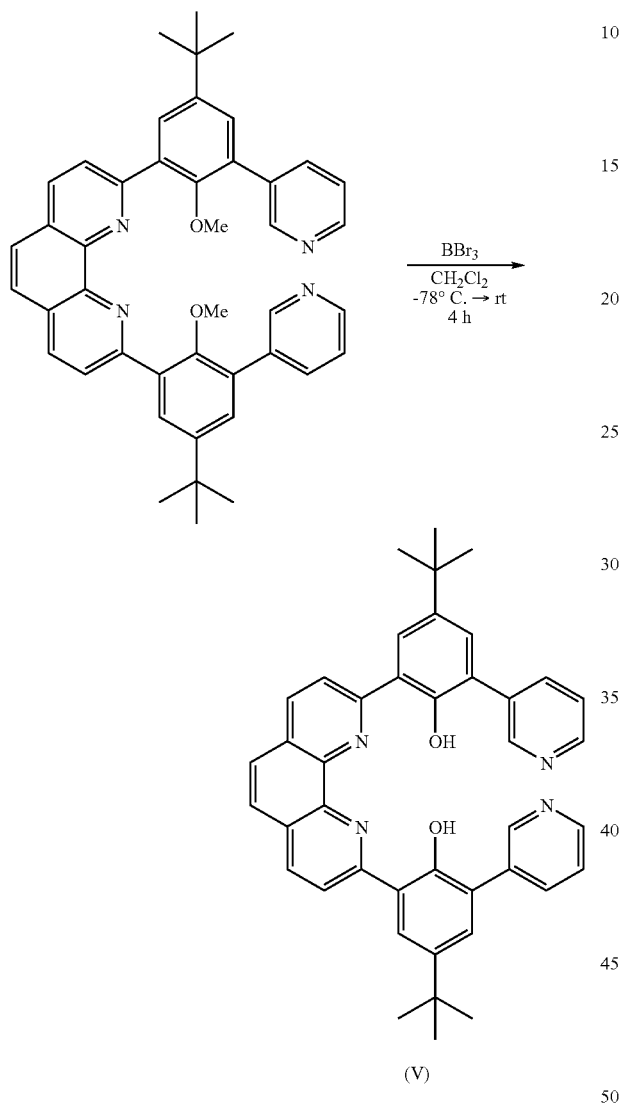

(V)

Under a nitrogen atmosphere, 0.110 g of Compound (U) was dissolved in 3 mL of anhydrous dichloromethane. While the dichloromethane solution was cooled to −78° C. in a dry ice/acetone bath, 1.3 mL of boron tribromide (1.0-M dichloromethane solution) was slowly dropped to the dichloromethane solution. After the dropping, the mixture was stirred for 10 minutes. Then, the dry ice/acetone bath was removed, and the mixture was left to stand while being stirred so that its temperature might reach room temperature. Four hours after that, the resultant was neutralized with a saturated aqueous solution of $NaHCO_3$, and then an organic layer was extracted three times by adding chloroform to the mixture. The obtained organic layer was concentrated, and the obtained residue was purified, whereby Ligand (V) was obtained.

$^1$H-NMR (300 MHz, $CDCl_3$) δ 1.47 (s, 18H), 7.44 (t, J=6.2 Hz, 2H), 7.55 (s, 2H), 7.95 (s, 2H), 8.16 (s, 2H), 8.40 (d, J=8.3 Hz, 2H), 8.53 (d, J=8.3 Hz, 2H), 8.67 (d, J=7.5 Hz, 2H), 9.47 (s, 2H), 9.79 (d, J=2.8 Hz, 2H), 15.36 (s, 2H)

Example 17

Synthesis of Metal Complex (W)

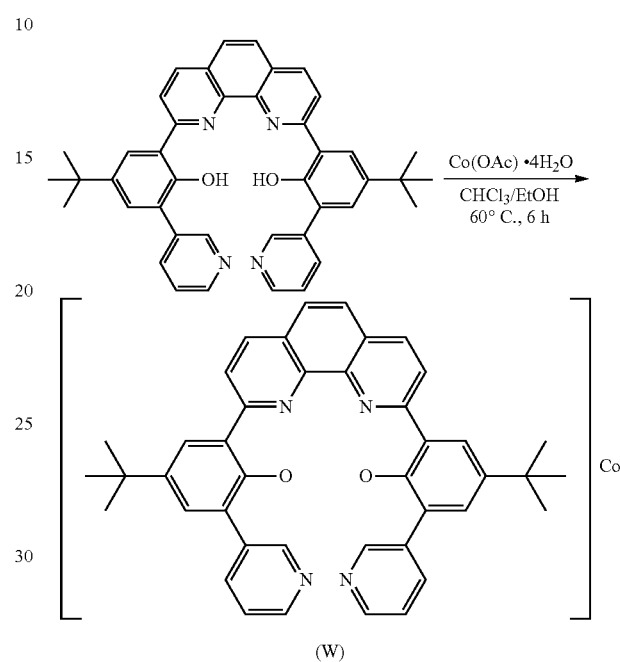

(W)

Under a nitrogen atmosphere, 0.096 g of Ligand (V) and mixed solution of 10 mL of chloroform and 4 mL of ethanol containing 0.037 g of cobalt acetate tetrahydrate were loaded into a 100-mL egg plant flask, and the mixture was stirred for 6 hours while being heated to 60° C., whereby a brown solid was produced. The solid was taken by filtration, and was then washed with ethanol and dried, whereby Metal Complex (W) was obtained (yield 0.040 g).

ESI-MS [M•]$^+$: 687.1

Figure 4:
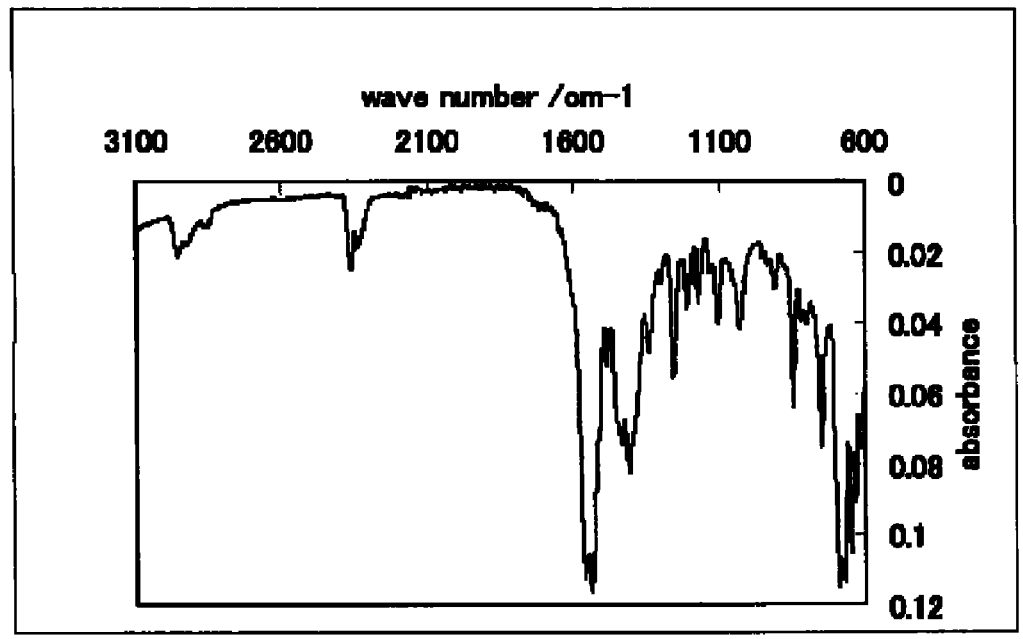
FIG. 4 shows an IR absorption spectrum of Metal Complex (W).

The infrared ray (IR) absorption spectrum of the obtained Metal Complex (W) is shown in FIG. 4.

Comparative Example 1

Synthesis of Metal Complex (X)

Metal Complex (X) was synthesized in accordance with the following reaction formula.

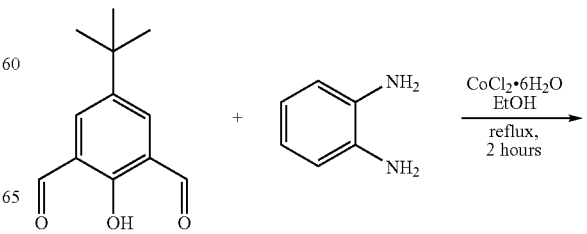

-continued

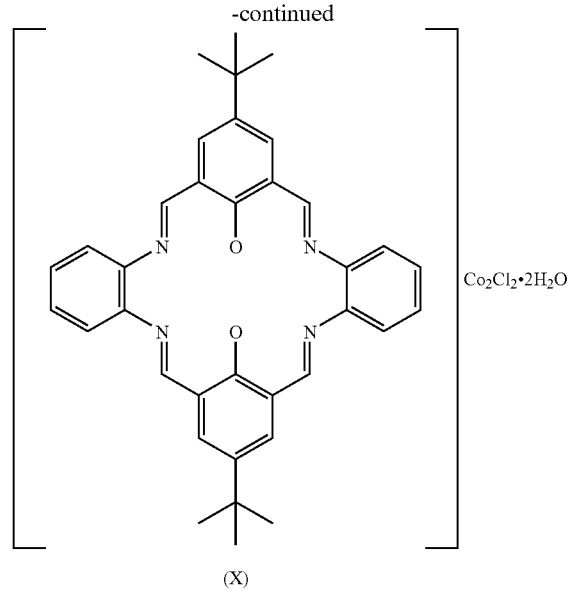

(X)

-continued

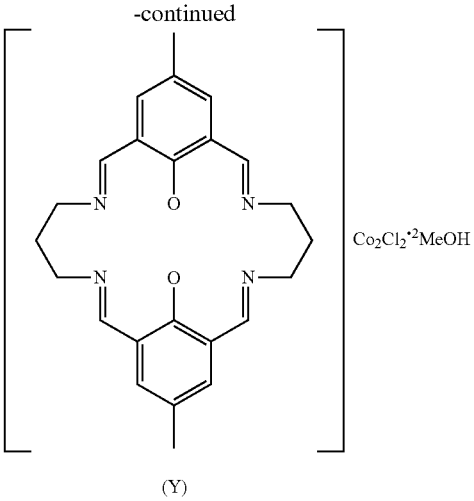

(Y)

First, under a nitrogen atmosphere, solution of 0.476 g of cobalt chloride hexahydrate and 0.412 g of 4-tert-butyl-2,6-diformylphenol in 10 mL of ethanol was charged into a 50-mL egg plant flask, and the solution was stirred at room temperature. Solution of 0.216 g of o-phenylenediamine in 5 mL of ethanol was gradually added to the solution. The above mixture was refluxed for 2 hours, whereby a brownish-red deposit was produced. The deposit was taken by filtration, and was then dried, whereby Metal Complex (X) was obtained (yield 0.465 g).

Elementary Analysis Value (%):

Calculated Value (Calcd for $C_{36}H_{38}Cl_2Co_2N_4O_4$); C, 55.47; H, 4.91; N, 7.19

Actual Measurement Value: C, 56.34; H, 4.83; N, 7.23

Comparative Example 2

Synthesis of Metal Complex (Y)

Metal Complex (Y) shown in the following reaction formula was synthesized in accordance with the method described in Australian Journal of Chemistry, 23, 2225 (1970).

First, under a nitrogen atmosphere, solution of 1.9 g of cobalt chloride hexahydrate and 1.31 g of 4-methyl-2,6-diformylphenol in 50 mL of methanol was charged into a 100-mL egg plant flask, and the solution was stirred at room temperature. Twenty milliliter of methanol containing 0.59 g of 1,3-propanediamine was gradually added to the solution. The above mixture was refluxed for 3 hours, whereby a brownish-red deposit was produced. The deposit was taken by filtration, and was then dried, whereby Metal Complex (Y) was obtained (yield 1.75 g).

Elementary Analysis Value (%):

Calculated Value (Calcd for $C_{26}H_{34}Cl_2Co_2N_4O_4$); C, 47.65; H, 5.23; N, 8.55

Actual Measurement Value: C, 46.64; H, 5.02; N, 8.58

Comparative Example 3

Synthesis of Metal Complex (Z)

Metal Complex (Z) shown in the following reaction formula was synthesized in accordance with the method described in Bulletin of Chemical Society of Japan, 68, 1105 (1995).

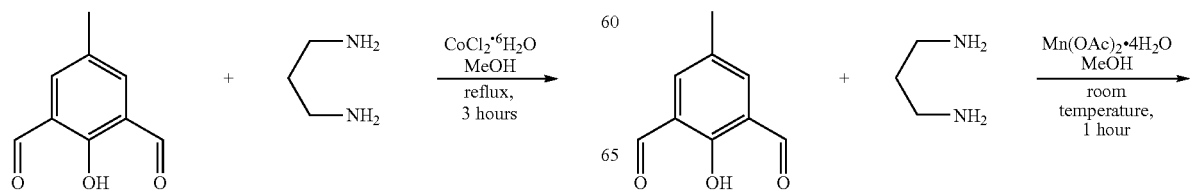

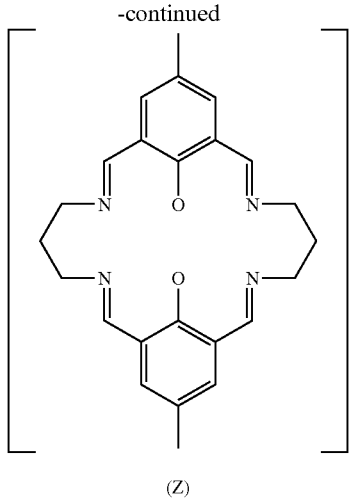

(Z)

Ten milliliter of methanol containing 0.33 g of 4-methyl-2,6-diformylphenol and 0.49 g of manganese acetate tetrahydrate was charged into a 50-mL egg plant flask, and the solution was stirred at room temperature. Five milliliter of methanol containing 0.15 g of 1,3-propanediamine was gradually added to the solution. The mixture was stirred for 1 hour, whereby a yellow deposit was produced. The produced precipitate was taken by filtration, washed with methanol, and dried in a vacuum, whereby Metal Complex (Z) was obtained (yield 0.25 g).

Elementary Analysis Value (%):
Calculated Value (Calcd for $C_{28}H_{32}Mn_2N_4O_6$); C, 53.34; H, 5.12; N, 8.89
Actual Measurement Value: C, 53.07; H, 5.12; N, 8.72

Comparative Example 4

Synthesis of Metal Complex (AA)

Metal Complex (AA) was synthesized by mixing chloroform containing a Schiff base ligand and ethanol containing cobalt acetate tetrahydrate and by causing them to react with each other in accordance with the following reaction formula. The Schiff base ligand as a raw material for the complex and Metal Complex (AA) were each synthesized in accordance with the method described in A chemistry, European Journal, 1999, 5, 1460.

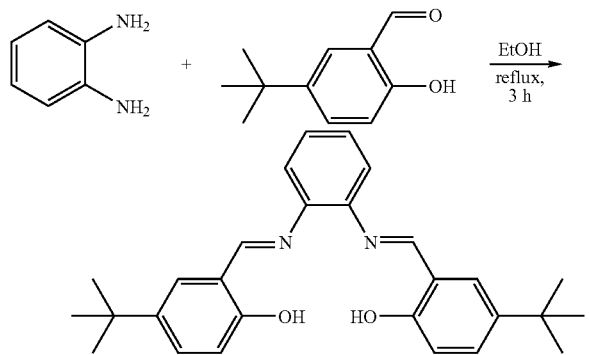

Under a nitrogen atmosphere, solution of 0.303 g of o-phenylenediamine and 1.00 g of 4-tert-butyl-2-formylphenol in 10 mL of ethanol was charged into a 50-mL egg plant flask, and the solution was stirred at 80° C. for 3 hours. The precipitated orange deposit was filtrated, washed, and dried, whereby the Schiff base ligand was obtained (yield 0.838 g).

$^1$H-NMR; δ: 12.83 (s, 2H), 8, 64 (s, 2H), 7.41 (d, 8.7 Hz, 2H), 7.36-7.32 (m, 4H), 7.25-7.21 (m, 4H), 6.99 (d: 8.7 Hz, 2H), 1.32 (s, 18H)

Subsequently, Metal Complex (AA) was synthesized by mixing chloroform containing the Schiff base ligand and ethanol containing cobalt acetate tetrahydrate and by causing them to react with each other.

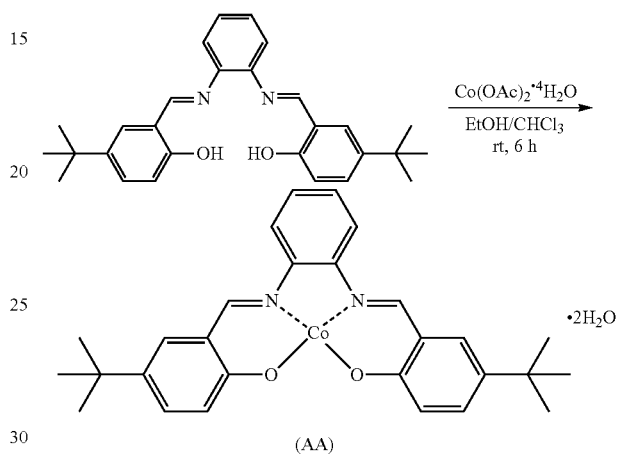

(AA)

Seven milliliter of ethanol containing 0.125 g of cobalt acetate tetrahydrate was added to a 25-mL egg plant flask containing solution of 0.214 g of the Schiff base ligand in 3 mL of chloroform while the chloroform solution was stirred. Then, the mixture was stirred at room temperature for 6 hours. The precipitated brown deposit was taken by filtration, washed with ethanol, and dried in a vacuum, whereby Metal Complex (AA) was obtained (yield 0.138 g).

Elementary Analysis Value (%):
Calcd for $C_{28}H_{34}CoN_2O_4$; C, 64.49; H, 6.57; N, 5.37. Found: C, 64.92; H, 6.13; N, 5.06.
ESI-MS [M•]$^+$: 485.1

Example 24

Acid Resistance Test of Metal Complex (A)

(1) Metal Complex (A) of the present invention was tested for its acid resistance with sulfuric acid. First, 7.90 mg of Metal Complex (A) were weighted and dissolved in 36 mL of methanol, and 9.0 mL of the solution were taken, and 1.0 mL of 1-M aqueous solution of sulfuric acid was added to the solution. After the mixture had been quickly stirred, 0.3 mL of the mixture was taken and diluted tenfold. The resultant solution was charged into a cell, and the cell was lidded. Then, the solution was heated to 60° C. A change in ultraviolet and visible absorption of the solution with time was observed with a spectrophotometer (Cary5E procuded by Varian, Inc.). Table 1 shows the absorbance at wavelength of 359 nm and ratios of the absorbance after certain time periods from immediately after the dropping. The results revealed that Metal Complex (A) of the present invention showed substantially no reduction in its absorbance even in the presence of an acid, and was hence excellent in stability.

TABLE 1

|  | Absorbance at 359 nm | Ratio of Absorbance |
| --- | --- | --- |
| Immediately after dropping | 0.457 | 1.00 |
| After 30 minutes | 0.477 | 1.00 |
| After 1 hour | 0.489 | 1.03 |
| After 2 hours | 0.497 | 1.04 |
| After 3 hours | 0.509 | 1.07 |

Example 25

Acid Resistance Test of Metal Complex (B)

The same operations as those described above were performed except that Metal Complex (A) was replaced with Metal Complex (B). Then, a change in UV absorption with time was observed. Table 2 shows the absorbance at wavelength of 444 nm and ratios of the absorbance after certain time periods from immediately after the dropping. The results revealed that Metal Complex (B) of the present invention showed substantially no reduction in its absorbance even in the presence of an acid, and was hence excellent in stability.

TABLE 2

|  | Absorbance at 444 nm | Ratio of Absorbance |
| --- | --- | --- |
| Immediately after dropping | 0.103 | 1.00 |
| After 30 minutes | 0.105 | 1.02 |
| After 1 hour | 0.104 | 1.02 |
| After 2 hours | 0.106 | 1.03 |
| After 3 hours | 0.108 | 1.05 |

Example 26

Acid Resistance Test of Metal Complex (D)

The same operations as those described above were performed except that Metal Complex (A) was replaced with Metal Complex (D). Then, a change in UV absorption with time was observed. Table 3 shows the absorbance at wavelength of 441 nm and ratios of the absorbance after certain time periods from immediately after the dropping. The results revealed that Metal Complex (D) of the present invention showed substantially no reduction in its absorbance even in the presence of an acid, and was hence excellent in stability.

TABLE 3

|  | Absorbance at 441 nm | Ratio of Absorbance |
| --- | --- | --- |
| Immediately after dropping | 0.075 | 1.00 |
| After 30 minutes | 0.075 | 1.00 |
| After 1 hour | 0.075 | 0.99 |
| After 2 hours | 0.077 | 1.02 |
| After 3 hours | 0.075 | 1.00 |

Example 27

Acid Resistance Test of Metal Complex (I)

The same operations as those described above were performed except that Metal Complex (A) was replaced with Metal Complex (I). Then, a change in UV absorption with time was observed. Table 4 shows the absorbance at wavelength of 547 nm and ratios of the absorbance after certain time periods from immediately after the dropping. The results revealed that Metal Complex (I) of the present invention showed substantially no reduction in its absorbance even in the presence of an acid, and was hence excellent in stability.

TABLE 4

|  | Absorbance at 547 nm | Ratio of Absorbance |
| --- | --- | --- |
| Immediately after dropping | 0.065 | 1.00 |
| After 30 minutes | 0.066 | 1.00 |
| After 1 hour | 0.067 | 1.03 |
| After 2 hours | 0.066 | 1.00 |
| After 3 hours | 0.072 | 1.10 |

Comparative Example 5

For comparison, the same operations as those described above were performed except that Metal Complex (A) was replaced with Metal Complex (X) in Comparative Example. Then, a change in UV absorption with time was observed. Table 5 shows the absorbance at wavelength of 455 nm and ratios of the absorbance after certain time periods from immediately after the dropping. Metal Complex (X) of Comparative Example showed a significant reduction in its absorbance with time in the presence of an acid, and was hence found to be decomposed.

TABLE 5

|  | Absorbance at 455 nm | Ratio of Absorbance |
| --- | --- | --- |
| Immediately after dropping | 0.363 | 1.00 |
| After 30 minutes | 0.366 | 1.01 |
| After 1 hour | 0.326 | 0.90 |
| After 2 hours | 0.265 | 0.73 |
| After 3 hours | 0.136 | 0.37 |

Example 28

Heat Resistance Test of Complex

A change in mass (TGA) of each of Metal Complexes (A), (B), (D), and (L) upon heat treatment of each metal complex in the range of 40 to 800° C. was measured with a thermogravimetric/differential thermal analyzer (EXSTAR-6300 produced by Seiko Instruments Inc.), and a mass reduction percentage was determined from a ratio to the initial metal complex subjected to the measurement. Conditions for the measurement were as follows: the measurement was performed under a nitrogen atmosphere in the range of 40 to 800° C. (at a rate of temperature increase of 10° C./min), and an alumina dish was used in the heat treatment. Table 6 shows the mass reduction percentage at 800° C.

Comparative Example 6

For comparison, the same experiment as that of Example 28 was performed with a thermogravimetric/differential thermal analyzer (EXSTAR-6300 produced by Seiko Instruments Inc.) except that Metal Complex (A) in Example 28 was replaced with Metal Complex (X), (Y), (Z), (AA), or (AB). Table 6 shows the mass reduction percentage. It should be noted that Metal Complex (AB) described above as a comparative example is an N,N'-disalicylalethylenediamine iron (II) complex (produced by TCI), which was used instead of Metal Complex (A) in Example 28.

Table 6 revealed that each of Metal Complexes (A), (B), (D), and (L) of the present invention showed a mass reduction percentage smaller than those of the metal complexes of comparative examples, which were of the same kind and were of the same nuclear number, and was hence excellent in heat resistance.

TABLE 6

|  | Mass Reduction Percentage at 800° C. (%) |
| --- | --- |
| Metal Complex (A) | 29.98 |
| Metal Complex (B) | 35.57 |
| Metal Complex (D) | 32.45 |
| Metal Complex (L) | 33.18 |
| Metal Complex (X) | 36.71 |
| Metal Complex (Y) | 50.41 |
| Metal Complex (Z) | 42.60 |
| Metal Complex (AA) | 58.00 |
| Metal Complex (AB) | 65.00 |

Example 29

Hydrogen Peroxide Decomposition Test of Metal Complex (D)

In a two-necked flask, 3.4 mg (about 8 μmol (per metal atom)) of Metal Complex (D) were weighed. A tartaric acid/sodium tartrate buffer solution (1.00 mL (prepared from 0.20-mol/L aqueous solution of tartaric acid and 0.10-mol/L aqueous solution of sodium tartrate, pH 4.0)) and ethylene glycol (1.00 mL) were added as solvents to the flask, and the mixture was stirred. The resultant was used as a catalyst mixed solution.

A septum was attached to one neck of the two-necked flask containing the catalyst mixed solution, and the other neck was coupled with a gas buret. After the flask had been stirred at 80° C. for 5 minutes, aqueous solution of hydrogen peroxide (11.4 mol/L, 0.20 mL (2.28 mmol)) was added to the solution with a syringe, and then a hydrogen peroxide decomposition reaction was performed at 80° C. for 20 minutes. The produced oxygen was measured with the gas buret, and the amount of decomposed hydrogen peroxide was determined.

The amount of decomposed hydrogen peroxide was determined from the volume of gases containing the oxygen produced by the hydrogen peroxide decomposition test. An actual volume v of the produced gases was converted into a gas volume V at 0° C. and 101,325 Pa (760 mmHg) taking a vapor pressure into consideration by using the following equation.

Figure 5:
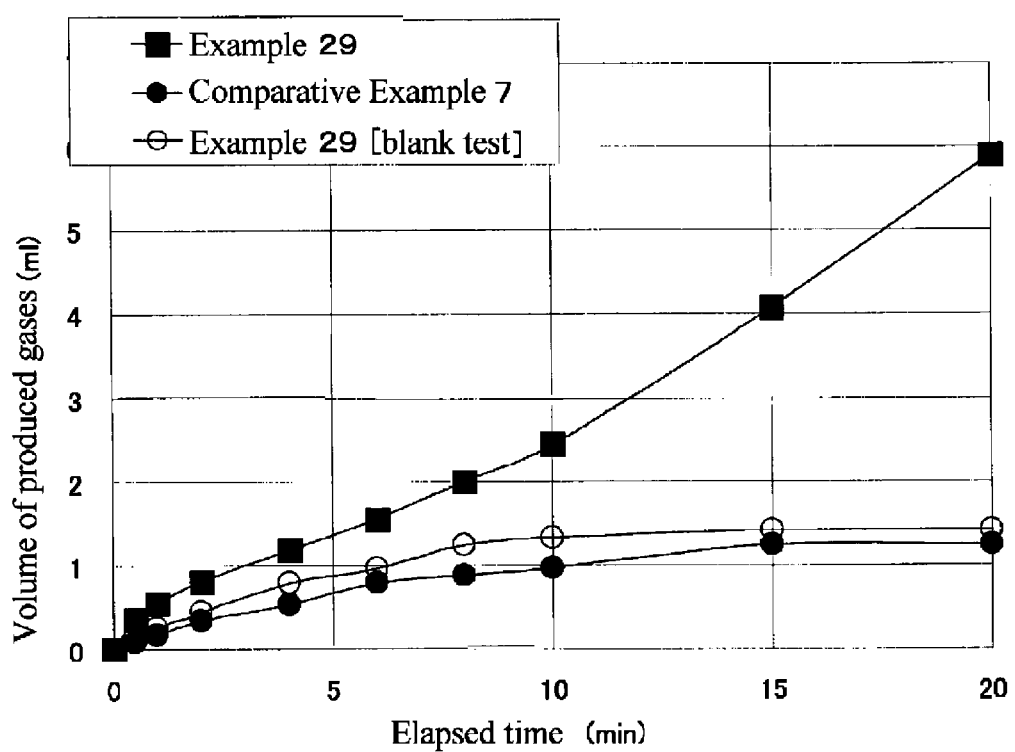
FIG. 5 shows results of hydrogen peroxide decomposition tests of Example 29 and Comparative Example 7.

FIG. 5 shows the results. Metal Complex (D) of the present invention led to the production of a larger volume of gases than that in the blank test to be described later, and hence its catalytic effect on the decomposition of hydrogen peroxide was confirmed.

$$V = \frac{273v(P-p)}{760(273+t))}$$

(In the formula, P represents an atmospheric pressure (mmHg), p represents a vapor pressure of water (mmHg), t represents a temperature (° C.), v represents an actual volume of the produced gases (mL), and V represents a gas volume (mL) at 0° C. and 101,325 Pa (760 mmHg).)

[Blank Test]

To a two-necked flask, 1.00 mL of buffer solution of aqueous solution of tartaric acid and sodium tartrate (prepared from 0.20-mol/L aqueous solution of tartaric acid and 0.10-mol/L aqueous solution of sodium tartrate, pH 4.0) and 1.00 mL of ethylene glycol were added as solvents. A septum was attached to one neck of the two-necked flask, and the other neck was coupled with a gas buret. After the flask had been stirred at 80° C. for 5 minutes, aqueous solution of hydrogen peroxide (11.4 mol/L, 0.200 mL (2.28 mmol)) was added to the solution, and the produced gases at 80° C. for 20 minutes was measured with the gas buret.

In the blank test, air and the like dissolved in the solution may be mainly detected.

Comparative Example 7

Hydrogen Peroxide Decomposition Test of Metal Complex (Z)

The same experiment as that of Example 29 was performed except that Metal Complex (D) of Example 29 was changed to Metal Complex (Z). FIG. 5 shows the results together with those of Example 29.

The volume of produced gases did not differ from that in the blank test, so the catalytic effect on the decomposition of hydrogen peroxide could not be confirmed.

INDUSTRIAL APPLICABILITY

The metal complex of the present invention is excellent in stability (such as heat resistance and acid resistance), and is hence useful as, for example, a redox reaction catalyst. Therefore, a reduction in the catalytic activity of the metal complex can be suppressed even at high temperatures or even in the presence of a strong acid, and the metal complex can be used in a wide variety of applications, so the metal complex is industrially useful.

Having described our invention as related to the present embodiments, it is our intention that the invention not be limited by any of the details of the description, unless otherwise specified, but rather be construed broadly within its spirit and scope as set out in the accompanying claims.

The invention claimed is:

1. A metal complex represented by the following formula (1):

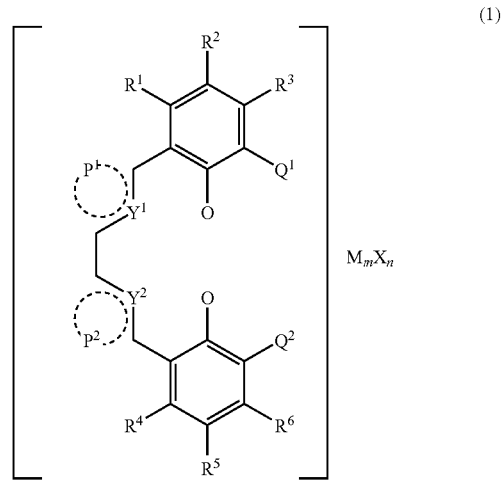

wherein $R^1$ to $R^6$ each independently represent a hydrogen atom or a substituent; $R^1$ and $R^2$, $R^2$ and $R^3$, $R^4$ and $R^5$, and/or R⁵ and R⁶ may be linked to each other to form a ring; and Y¹ and Y² each independently represent any one of the following groups:

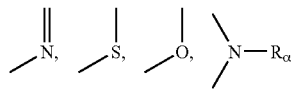

wherein R_α represents a hydrogen atom or a hydrocarbon group having 1 to 4 carbon atoms; P¹ represents a group of atoms necessary for forming a heterocyclic ring together with Y¹ and the two carbon atoms at a position adjacent to Y¹; P² represents a group of atoms necessary for forming a heterocyclic ring together with Y² and the two carbon atoms at a position adjacent to Y²; P¹ and P² may be linked to each other, to form a ring; m represents 1 or 2; when m is 1, M represents aluminum, titanium, vanadium, chromium, manganese, iron, cobalt, nickel, copper, zinc, gallium, germanium, zirconium, niobium, molybdenum, ruthenium, rhodium, palladium, silver, cadmium, indium, tin, antimony, tantalum, tungsten, rhenium, osmium, iridium, platinum, or gold; when m is 2, two M's may be the same as or different from each other, and M represents a transition metal element belonging to Groups 3 to 9 described in the periodic table; X represents a counter ion or a neutral molecule; n represents the number of X's in the complex, and an integer of 0 or more; when a plurality of X's are present, the X's may be the same as or different from each other; and Q¹ and Q² each independently represent an aromatic heterocyclic group.

2. The metal complex according to claim 1, wherein, in the formula (1), m represents 2.

3. The metal complex according to claim 1, wherein, in the formula (1), m represents 1.

4. A catalyst, comprising the metal complex according to claim 1.

5. The metal complex according to claim 1, wherein, in the formula (1), the substituent represented by any of R¹ to R⁶ is a halogeno group, a linear or branched saturated hydrocarbon group having 1 to 20 carbon atoms in total, a linear or branched alkoxy group having 1 to 10 carbon atoms in total, or an aromatic group having 6 to 30 carbon atoms in total.

6. The metal complex according to claim 1, wherein, in the formula (1), the heterocyclic ring formed by P¹ and Y¹ together with the two carbon atoms adjacent to Y¹, and the heterocyclic ring formed by P² and Y² together with the two carbon atoms adjacent to Y², each are pyridine, pyrazine, pyrimidine, pyrrole, N-alkyl pyrrole, furan, thiophene, thiazole, imidazole, oxazole, benzimidazole, benzofuran, benzothiophene, isoquinoline, or quinazoline, which heterocyclic ring may be substituted by a halogeno group, a linear or branched saturated hydrocarbon group having 1 to 20 carbon atoms in total, a linear or branched alkoxy group having 1 to 10 carbon atoms in total, or an aromatic group having 6 to 30 carbon atoms in total, as a substituent on the heterocyclic ring.

7. The metal complex according to claim 1, wherein, in the formula (1), the ring formed by P¹ and P² bonded together is a structure represented by any one of the following formulae (1-a) to (1-i):

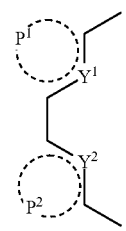

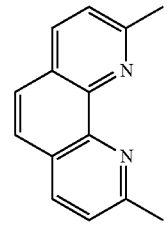
(1-a)

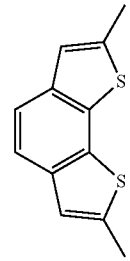
(1-b)

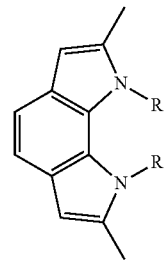
(1-c)

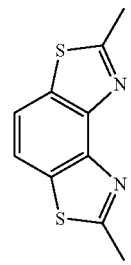
(1-d)

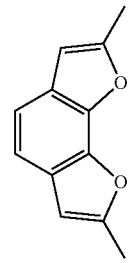
(1-e)

-continued (1-f)
(1-g)
(1-h)
(1-i)

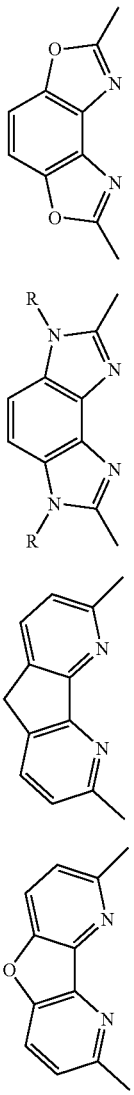

in which R represents a hydrogen atom or a hydrocarbon group having 1 to 30 carbon atoms, which ring formed by $P^1$ and $P^2$ bonded together may be substituted by a halogeno group, a linear or branched saturated hydrocarbon group having 1 to 20 carbon atoms in total, a linear or branched alkoxy group having 1 to 10 carbon atoms in total, or an aromatic group having 6 to 30 carbon atoms in total, as a substituent on the ring.

8. The metal complex according to claim 1, wherein, in the formula (1), the aromatic heterocyclic group represented by $Q^1$ or $Q^2$ is a pyridyl group, a pyrazyl group, a pyrimidyl group, a pyridazyl group, a pyrrolyl group, a furyl group, a thienyl group, a thiazolyl group, an imidazolyl group, an oxazolyl group, a triazolyl group, an indolyl group, a benzoimidazolyl group, a benzofuryl group, a benzothienyl group, a quinolyl group, an isoquinolyl group, a cinnolyl group, a phthalazyl group, a quinazolyl group, a quinoxanyl group, or a benzodiazyl group, which aromatic heterocyclic group represented by $Q^1$ or $Q^2$ may be substituted by a halogeno group, a linear or branched saturated hydrocarbon group having 1 to 20 carbon atoms in total, a linear or branched alkoxy group having 1 to 10 carbon atoms in total, or an aromatic group having 6 to 30 carbon atoms in total, as a substituent on the aromatic heterocyclic group.

9. A metal complex represented by the following formula (2):

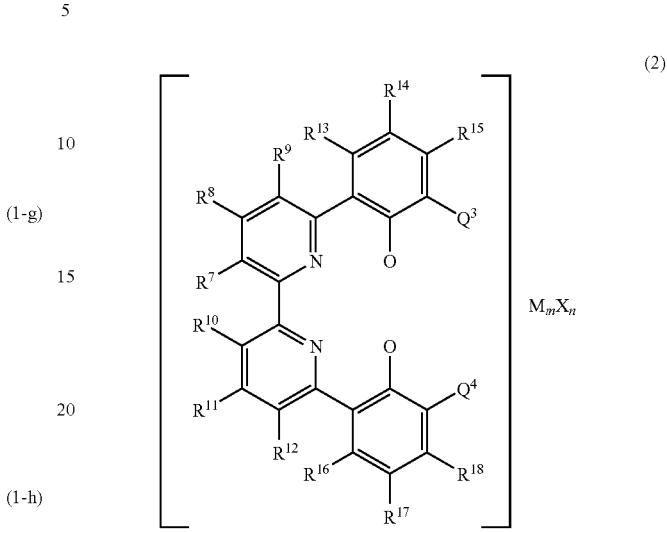

(2)

wherein $R^7$ to $R^{18}$ each independently represent a hydrogen atom or a substituent; $R^7$ and $R^{10}$, $R^7$ and $R^8$, $R^8$ and $R^9$, $R^9$ and $R^{13}$, $R^{10}$ and $R^{11}$, $R^{11}$ and $R^{12}$, $R^{12}$ and $R^{16}$, $R^{13}$ and $R^{14}$, $R^{14}$ and $R^{15}$, $R^{16}$ and $R^{17}$ and/or $R^{17}$ and $R^{18}$ may be linked to each other, to form a ring; m represents 1 or 2; when m is 1, M represents aluminum, titanium, vanadium, chromium, manganese, iron, cobalt, nickel, copper, zinc, gallium, germanium, zirconium, niobium, molybdenum, ruthenium, rhodium, palladium, silver, cadmium, indium, tin, antimony, tantalum, tungsten, rhenium, osmium, iridium, platinum, or gold; when m is 2, two M's may be the same as or different from each other, and M represents a transition metal element belonging to Groups 3 to 9 described in the periodic table; X represents a counter ion or a neutral molecule; n represents the number of X's in the complex, and an integer of 0 or more; when a plurality of X's are present, the X's may be the same as or different from each other; and $Q^3$ and $Q^4$ each independently represent an aromatic heterocyclic group.

10. The metal complex according to claim 9, wherein, in the formula (2), m represents 2.

11. The metal complex according to claim 9, wherein, in the formula (2), m represents 1.

12. A catalyst, comprising the metal complex according to claim 9.

13. The metal complex according to claim 9, wherein, in the formula (2), the substituent represented by any of $R^7$ to $R^{18}$ is a halogeno group, a linear or branched saturated hydrocarbon group having 1 to 20 carbon atoms in total, a linear or branched alkoxy group having 1 to 10 carbon atoms in total, or an aromatic group having 6 to 30 carbon atoms in total.

14. The metal complex according to claim 9, wherein, in the formula (2), the aromatic heterocyclic group represented by $Q^3$ or $Q^4$ is a pyridyl group, a pyrazyl group, a pyrimidyl group, a pyridazyl group, a pyrrolyl group, a furyl group, a thienyl group, a thiazolyl group, an imidazolyl group, an oxazolyl group, a triazolyl group, an indolyl group, a benzoimidazolyl group, a benzofuryl group, a benzothienyl group, a quinolyl group, an isoquinolyl group, a cinnolyl group, a phthalazyl group, a quinazolyl group, a quinoxanyl group, or a benzodiazyl group, which aromatic heterocyclic group represented by $Q^3$ or $Q^4$ may be substituted by a halogeno group, a linear or branched saturated hydrocarbon group having 1 to 20 carbon atoms in total, a linear or branched alkoxy group having 1 to 10 carbon atoms in total, or an aromatic group having 6 to 30 carbon atoms in total, as a substituent on the aromatic heterocyclic group.

15. A polymer, comprising a residue of a metal complex represented by the following formula (1):

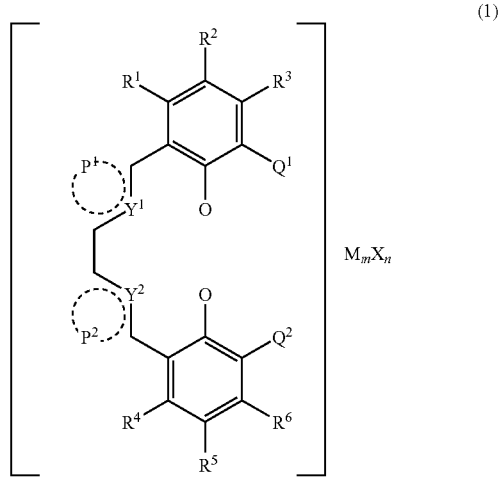
(1)

wherein $R^1$ to $R^6$ each independently represent a hydrogen atom or a substituent; $R^1$ and $R^2$, $R^2$ and $R^3$, $R^4$ and $R^5$, and/or $R^5$ and $R^6$ may be linked to each other to form a ring; and $Y^1$ and $Y^2$ each independently represent any one of the following groups:

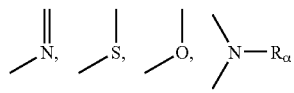

wherein $R_\alpha$ represents a hydrogen atom or a hydrocarbon group having 1 to 4 carbon atoms; $P^1$ represents a group of atoms necessary for forming a heterocyclic ring together with $Y^1$ and the two carbon atoms at a position adjacent to $Y^1$; $P^2$ represents a group of atoms necessary for forming a heterocyclic ring together with $Y^2$ and the two carbon atoms at a position adjacent to $Y^2$; $P^1$ and $P^2$ may be linked to each other to form a ring; m represents 1 or 2; when m is 1, M represents aluminum, titanium, vanadium, chromium, manganese, iron, cobalt, nickel, copper, zinc, gallium, germanium, zirconium, niobium, molybdenum, ruthenium, rhodium, palladium, silver, cadmium, indium, tin, antimony, tantalum, tungsten, rhenium, osmium, iridium, platinum, or gold; when m is 2, two M's may be the same as or different from each other, and M represents a transition metal element belonging to Groups 3 to 9 described in the periodic table; X represents a counter ion or a neutral molecule; n represents the number of X's in the complex, and an integer of 0 or more; when a plurality of X's are present, the X's may be the same as or different from each other; and $Q^1$ and $Q^2$ each independently represent an aromatic heterocyclic group.

16. The polymer according to claim 15, comprising the residue of the metal complex represented by the formula (1) as a repeating unit.

17. A catalyst, comprising the polymer according to claim 15.

18. A polymer, comprising a residue of a metal complex represented by the following formula (2):

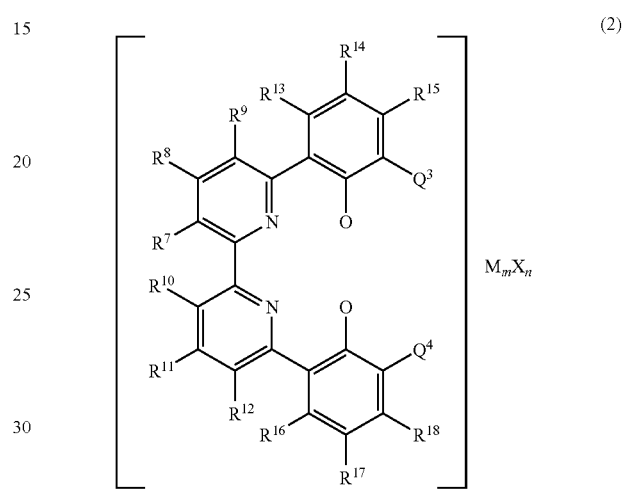
(2)

wherein $R^7$ to $R^{18}$ each independently represent a hydrogen atom or a substituent; $R^7$ and $R^{10}$, $R^7$ and $R^8$, $R^8$ and $R^9$, $R^9$ and $R^{13}$, $R^{10}$ and $R^{11}$, $R^{11}$ and $R^{12}$, $R^{12}$ and $R^{16}$, $R^{13}$ and $R^{14}$, $R^{14}$ and $R^{15}$, $R^{16}$ and $R^{17}$ and/or $R^{17}$ and $R^{18}$ may be linked to each other to form a ring; m represents 1 or 2; when m is 1, M represents aluminum, titanium, vanadium, chromium, manganese, iron, cobalt, nickel, copper, zinc, gallium, germanium, zirconium, niobium, molybdenum, ruthenium, rhodium, palladium, silver, cadmium, indium, tin, antimony, tantalum, tungsten, rhenium, osmium, iridium, platinum, or gold; when m is 2, two M's may be the same as or different from each other, and M represents a transition metal element belonging to Groups 3 to 9 described in the periodic table; X represents a counter ion or a neutral molecule; n represents the number of X's in the complex, and an integer of 0 or more; when a plurality of X's are present, the X's may be the same as or different from each other; and $Q^3$ and $Q^4$ each independently represent an aromatic heterocyclic group.

19. The polymer according to claim 18, comprising the residue of the metal complex represented by the formula (2) as a repeating unit.

20. A catalyst, comprising the polymer according to claim 18.

* * * * *